（12） United States Patent
de Canniere et al.

(10) Patent No.: US 10,813,630 B2
(45) Date of Patent: Oct. 27, 2020

(54) CLOSURE SYSTEM FOR ATRIAL WALL

(71) Applicant: CorQuest Medical, Inc., Aventura, FL (US)

(72) Inventors: Didier de Canniere, Miami Beach, FL (US); Khanh Tran Duy, Walhain (BE)

(73) Assignee: CorQuest Medical, Inc., Aventura, FL (US)

( * ) Notice: Subject to any disclaimer, the term of this patent is extended or adjusted under 35 U.S.C. 154(b) by 769 days.

(21) Appl. No.: 14/065,613

(22) Filed: Oct. 29, 2013

(65) Prior Publication Data

US 2015/0039023 A1 Feb. 5, 2015

Related U.S. Application Data

(63) Continuation-in-part of application No. 13/838,199, filed on Mar. 15, 2013, now Pat. No. 10,307,167, and
(Continued)

(51) Int. Cl.
*A61B 17/00* (2006.01)
*A61B 17/12* (2006.01)

(52) U.S. Cl.
CPC ...... *A61B 17/0057* (2013.01); *A61B 17/1214* (2013.01); *A61B 17/12122* (2013.01);
(Continued)

(58) Field of Classification Search
CPC .......... A61B 17/0057; A61B 17/12122; A61B 2017/00575; A61B 2017/00623; A61B 2017/12054
See application file for complete search history.

(56) References Cited

U.S. PATENT DOCUMENTS 3,587,567 A 6/1971 Schiff
4,536,893 A 8/1985 Parravicini
(Continued)

FOREIGN PATENT DOCUMENTS

EP 0577400 B1 10/1999
EP 1147743 10/2001
(Continued)

OTHER PUBLICATIONS

Mike Blaber, Metals, Non-Metals, and Metalloids, http://www.mikeblaber.org/oldwine/chm 1045/notes/Periodic/Metals/Period06.htm, 1996, accessed May 14, 2015.
(Continued)

*Primary Examiner* — Sarah A Simpson
(74) *Attorney, Agent, or Firm* — Ferguson Case Orr Paterson

(57) ABSTRACT

A closure system, assembly and attended method for closing and opening in the tissue of the patient includes first and second closure members each including a biased construction operative for disposition of the closure members into an out of retracted and expanded orientations. A connector is disposed in interconnecting relation with the closure members and structured to establish at least a partial spacing there between. The biased construction and the interconnection of the closure members facilitate con current disposition of the closure members with one another into and through an introductory instrument as well as independent and successive disposition of the first and second closure members into a closing relation to the tissue opening upon exiting the introductory instrument.

23 Claims, 22 Drawing Sheets

Related U.S. Application Data a continuation-in-part of application No. 13/714,989, filed on Dec. 14, 2012, now Pat. No. 10,314,594, application No. 13/838,199, which is a continuation-in-part of application No. 13/570,347, filed on Aug. 9, 2012, now abandoned, which is a continuation-in-part of application No. 13/442,230, filed on Apr. 9, 2012, now abandoned.

(60) Provisional application No. 61/574,798, filed on Aug. 9, 2011.

(52) U.S. Cl.
CPC .. *A61B 17/12168* (2013.01); *A61B 17/12177* (2013.01); *A61B 2017/00575* (2013.01); *A61B 2017/00592* (2013.01); *A61B 2017/00597* (2013.01); *A61B 2017/00623* (2013.01); *A61B 2017/00632* (2013.01); *A61B 2017/12054* (2013.01)

(56) References Cited

U.S. PATENT DOCUMENTS

| | | |
|---|---|---|
| 4,690,134 A | 9/1987 | Snyders |
| 4,809,694 A | 3/1989 | Ferrara |
| 5,201,742 A | 4/1993 | Hasson |
| 5,591,170 A | 1/1997 | Spievack et al. |
| 5,702,421 A | 12/1997 | Schneidt |
| 5,924,424 A | 7/1999 | Stevens et al. |
| 6,063,070 A | 5/2000 | Eder |
| 6,123,084 A | 9/2000 | Jandak et al. |
| 6,206,907 B1 | 3/2001 | Marino et al. |
| 6,328,757 B1 | 12/2001 | Matheny |
| 6,383,174 B1 | 5/2002 | Eder |
| 6,425,911 B1 | 7/2002 | Akerfeldt et al. |
| 6,508,828 B1 | 1/2003 | Akerfeldt et al. |
| 6,537,290 B2 | 3/2003 | Adams et al. |
| 6,596,012 B2 | 7/2003 | Akerfeldt et al. |
| 6,616,596 B1 | 9/2003 | Milbocker |
| 6,641,592 B1 | 11/2003 | Sauer |
| 6,682,489 B2 | 1/2004 | Tenerz et al. |
| 6,712,837 B2 | 3/2004 | Åkerfeldt et al. |
| 6,802,851 B2 | 10/2004 | Jones et al. |
| 6,811,560 B2 | 11/2004 | Jones et al. |
| 6,902,522 B1 | 6/2005 | Walsh |
| 6,929,655 B2 | 8/2005 | Egnelöv et al. |
| 6,958,044 B2 | 10/2005 | Burbank et al. |
| 6,960,220 B2 | 11/2005 | Marino et al. |
| 7,044,916 B2 | 5/2006 | Tenerz et al. |
| 7,445,626 B2 | 11/2008 | Songer |
| 7,854,743 B2 | 12/2010 | Palasis et al. |
| 8,092,363 B2 | 1/2012 | Leinsing |
| 8,133,168 B2 | 3/2012 | Monnet |
| 8,147,542 B2 | 4/2012 | Maisano et al. |
| 8,408,214 B2 | 4/2013 | Spenser |
| 8,506,624 B2 | 8/2013 | Vidlund |
| 8,758,393 B2 | 6/2014 | Zentgraf |
| 8,790,394 B2 | 7/2014 | Miller |
| 9,566,443 B2 | 2/2017 | de Cannier |
| 2002/0058925 A1 | 5/2002 | Kaplan et al. |
| 2002/0100485 A1 | 8/2002 | Stevens et al. |
| 2002/0161378 A1 | 10/2002 | Downing |
| 2002/0183787 A1* | 12/2002 | Wahr ............... A61B 17/0057 606/213 |
| 2003/0120337 A1 | 6/2003 | Van Tassel et al. |
| 2004/0087831 A1 | 5/2004 | Michels et al. |
| 2004/0102804 A1 | 5/2004 | Chin |
| 2004/0106945 A1 | 6/2004 | Thramann et al. |
| 2004/0116897 A1 | 6/2004 | Aboul-Hosn |
| 2004/0138526 A1 | 7/2004 | Guenst |
| 2004/0138527 A1 | 7/2004 | Bonner et al. |
| 2004/0143277 A1 | 7/2004 | Marino et al. |
| 2005/0137700 A1 | 6/2005 | Spence |
| 2005/0149108 A1 | 7/2005 | Cox |
| 2006/0074484 A1 | 4/2006 | Huber |
| 2006/0135962 A1 | 6/2006 | Kick et al. |
| 2006/0241655 A1 | 10/2006 | Viola |
| 2006/0247672 A1 | 11/2006 | Vidlund et al. |
| 2007/0055206 A1 | 3/2007 | To |
| 2007/0135826 A1 | 6/2007 | Zaver et al. |
| 2007/0162066 A1 | 7/2007 | Lyon |
| 2007/0239108 A1 | 10/2007 | Albrecht et al. |
| 2007/0265643 A1 | 11/2007 | Beane et al. |
| 2008/0033241 A1 | 2/2008 | Peh et al. |
| 2008/0114342 A1 | 5/2008 | Whayne et al. |
| 2008/0140116 A1 | 6/2008 | Bonutti |
| 2008/0249420 A1 | 10/2008 | Crossman |
| 2008/0275295 A1 | 11/2008 | Gertner |
| 2008/0281350 A1 | 11/2008 | Sepetka et al. |
| 2009/0005800 A1 | 1/2009 | Franer |
| 2009/0105751 A1 | 4/2009 | Zentgraf |
| 2009/0182188 A1 | 7/2009 | Marseille et al. |
| 2009/0192598 A1 | 7/2009 | Lattouf |
| 2010/0042147 A1 | 2/2010 | Janovsky et al. |
| 2010/0161042 A1 | 6/2010 | Maisano et al. |
| 2010/0161043 A1 | 6/2010 | Maisano |
| 2010/0179574 A1 | 7/2010 | Longoria et al. |
| 2010/0228077 A1 | 9/2010 | Lenker et al. |
| 2010/0274091 A1 | 10/2010 | Rothstein et al. |
| 2010/0324586 A1 | 12/2010 | Miles et al. |
| 2011/0029071 A1 | 2/2011 | Zlotnick et al. |
| 2011/0060182 A1 | 3/2011 | Kassab et al. |
| 2011/0137234 A1 | 6/2011 | Farnan et al. |
| 2011/0166413 A1 | 7/2011 | Alferness |
| 2011/0184439 A1* | 7/2011 | Anderson .......... A61B 17/0057 606/151 |
| 2011/0190811 A1 | 8/2011 | Shanley |
| 2012/0278236 A1 | 1/2012 | Jain et al. |
| 2012/0029556 A1* | 2/2012 | Masters ............. A61B 17/0057 606/213 |
| 2012/0143209 A1 | 6/2012 | Brecheen et al. |
| 2012/0238968 A1 | 9/2012 | Toy et al. |
| 2012/0245416 A1 | 9/2012 | Viola |
| 2012/0272452 A1 | 11/2012 | Schultz |
| 2012/0272495 A1 | 11/2012 | Hildebrandt et al. |
| 2012/0272497 A1 | 11/2012 | Smith |
| 2012/0272499 A1 | 11/2012 | Schley et al. |
| 2012/0272523 A1 | 11/2012 | Calla et al. |
| 2012/0272555 A1 | 11/2012 | Heath |
| 2012/0272556 A1 | 11/2012 | Brown |
| 2012/0272595 A1 | 11/2012 | Gallant |
| 2012/0272603 A1 | 11/2012 | Carbines |
| 2012/0272611 A1 | 11/2012 | Tsukimoto et al. |
| 2012/0272624 A1 | 11/2012 | Argeriou et al. |
| 2012/0272632 A1 | 11/2012 | Lans |
| 2012/0272637 A1 | 11/2012 | Holland et al. |
| 2012/0272652 A1 | 11/2012 | Nicholls et al. |
| 2012/0272653 A1 | 11/2012 | Merrill et al. |
| 2012/0272660 A1 | 11/2012 | Garrett |
| 2012/0272661 A1 | 11/2012 | Milburn |
| 2012/0272662 A1 | 11/2012 | Milburn |
| 2012/0272667 A1 | 11/2012 | Ferraro et al. |
| 2012/0272670 A1 | 11/2012 | Choi et al. |
| 2012/0272705 A1 | 11/2012 | Hirane |
| 2012/0272738 A1 | 11/2012 | Klessel et al. |
| 2012/0272741 A1 | 11/2012 | Xiao et al. |
| 2012/0272768 A1 | 11/2012 | Schmidt et al. |
| 2012/0272780 A1 | 11/2012 | Schimings et al. |
| 2012/0272815 A1 | 11/2012 | Lingel et al. |
| 2012/0272817 A1 | 11/2012 | Lindh, Sr. et al. |
| 2012/0272841 A1 | 11/2012 | Heymanns et al. |
| 2012/0272843 A1 | 11/2012 | Graff |
| 2012/0272845 A1 | 11/2012 | Loiret-Bernal et al. |
| 2012/0272846 A1 | 11/2012 | Fleischer et al. |
| 2012/0272876 A1 | 11/2012 | Bergeron et al. |
| 2012/0272893 A1 | 11/2012 | Lauerhaas et al. |
| 2012/0272968 A1 | 11/2012 | Kirschner |
| 2012/0272996 A1 | 11/2012 | Jimenez et al. |
| 2012/0273014 A1 | 11/2012 | Tadayon |
| 2012/0273064 A1 | 11/2012 | Ismert et al. |
| 2012/0273078 A1 | 11/2012 | Hawwa et al. |
| 2012/0273079 A1 | 11/2012 | Guclucan |
| 2012/0273141 A1 | 11/2012 | Miller et al. |

(56) References Cited

U.S. PATENT DOCUMENTS

| | | |
|---|---|---|
| 2012/0273142 A1 | 11/2012 | Miller et al. |
| 2012/0273143 A1 | 11/2012 | Fillmore et al. |
| 2012/0273161 A1 | 11/2012 | Raver |
| 2012/0273174 A1 | 11/2012 | Barnes |
| 2012/0273178 A1 | 11/2012 | Wanni et al. |
| 2012/0273209 A1 | 11/2012 | Austin et al. |
| 2012/0273210 A1 | 11/2012 | Arizmendi, Jr. et al. |
| 2012/0273214 A1 | 11/2012 | Donald et al. |
| 2012/0273219 A1 | 11/2012 | Hoffman et al. |
| 2012/0273220 A1 | 11/2012 | Ezekiel et al. |
| 2012/0273228 A1 | 11/2012 | Allouche |
| 2012/0273230 A1 | 11/2012 | Patterson et al. |
| 2012/0273231 A1 | 11/2012 | Whiddon |
| 2012/0273232 A1 | 11/2012 | O'Blenes |
| 2012/0273328 A1 | 11/2012 | Sejourne |
| 2012/0273358 A1 | 11/2012 | Larnoy et al. |
| 2012/0273389 A1 | 11/2012 | Aziz et al. |
| 2012/0273399 A1 | 11/2012 | Daboub et al. |
| 2012/0273438 A1 | 11/2012 | Nordin et al. |
| 2012/0273439 A1 | 11/2012 | Beavers et al. |
| 2012/0273458 A1 | 11/2012 | Bret et al. |
| 2012/0273467 A1 | 11/2012 | Baxter et al. |
| 2012/0273470 A1 | 11/2012 | Zediker et al. |
| 2012/0273518 A1 | 11/2012 | Greer, Jr. |
| 2012/0273555 A1 | 11/2012 | Flak et al. |
| 2012/0273580 A1 | 11/2012 | Warren et al. |
| 2012/0273641 A1 | 11/2012 | Gorman et al. |
| 2012/0273647 A1 | 11/2012 | Moruazi |
| 2012/0273680 A1 | 11/2012 | Furry |
| 2012/0273843 A1 | 11/2012 | Kim |
| 2012/0273860 A1 | 11/2012 | Chen et al. |
| 2012/0273880 A1 | 11/2012 | Teng et al. |
| 2012/0273902 A1 | 11/2012 | Lin et al. |
| 2012/0273955 A1 | 11/2012 | Or-Bach et al. |
| 2012/0273987 A1 | 11/2012 | Belcher et al. |
| 2012/0273989 A1 | 11/2012 | Graf |
| 2012/0273993 A1 | 11/2012 | Shoseyov et al. |
| 2012/0274001 A1 | 11/2012 | Prabhu |
| 2012/0274020 A1 | 11/2012 | Daboub |
| 2012/0274061 A1 | 11/2012 | Wilkinson |
| 2012/0274065 A1 | 11/2012 | Knapp |
| 2012/0274068 A1 | 11/2012 | Hanback |
| 2012/0274076 A1 | 11/2012 | Kelaiditis et al. |
| 2012/0274145 A1 | 11/2012 | Taddeo |
| 2012/0274198 A1 | 11/2012 | Jenek |
| 2012/0274202 A1 | 11/2012 | Komatsu |
| 2012/0274212 A1 | 11/2012 | Yu et al. |
| 2012/0274256 A1 | 11/2012 | O'Rourke |
| 2012/0274266 A1 | 11/2012 | Yip |
| 2012/0274279 A1 | 11/2012 | Banos et al. |
| 2012/0274280 A1 | 11/2012 | Yip et al. |
| 2012/0274281 A1 | 11/2012 | Kim |
| 2012/0274288 A1 | 11/2012 | Wegener |
| 2012/0274332 A1 | 11/2012 | Sinha et al. |
| 2012/0274391 A1 | 11/2012 | Kim |
| 2012/0274395 A1 | 11/2012 | Deam |
| 2012/0274440 A1 | 11/2012 | Meadows et al. |
| 2012/0274470 A1 | 11/2012 | Sandvick |
| 2012/0274477 A1 | 11/2012 | Prammer |
| 2012/0274769 A1 | 11/2012 | Lee |
| 2012/0274770 A1 | 11/2012 | Lee |
| 2012/0274772 A1 | 11/2012 | Fosburgh et al. |
| 2012/0274870 A1 | 11/2012 | Liu |
| 2012/0274937 A1 | 11/2012 | Hays et al. |
| 2012/0274962 A1 | 11/2012 | Thomas et al. |
| 2012/0275056 A1 | 11/2012 | McGuire, Jr. |
| 2012/0275057 A1 | 11/2012 | McGuire, Jr. |
| 2012/0275085 A1 | 11/2012 | Wilson et al. |
| 2012/0275128 A1 | 11/2012 | Takada et al. |
| 2012/0275140 A1 | 11/2012 | Feinbloom et al. |
| 2012/0275236 A1 | 11/2012 | Hess et al. |
| 2012/0275244 A1 | 11/2012 | Do |
| 2012/0275247 A1 | 11/2012 | Hwang et al. |
| 2012/0275248 A1 | 11/2012 | Won |
| 2012/0275249 A1 | 11/2012 | Yang et al. |
| 2012/0275298 A1 | 11/2012 | Bryant et al. |
| 2012/0275299 A1 | 11/2012 | Taylor et al. |
| 2012/0275338 A1 | 11/2012 | Filsfils et al. |
| 2012/0275356 A1 | 11/2012 | Aharony et al. |
| 2012/0275670 A1 | 11/2012 | Joglekar |
| 2012/0275754 A1 | 11/2012 | Krampotich et al. |
| 2012/0275841 A1 | 11/2012 | Jimenez et al. |
| 2012/0275843 A1 | 11/2012 | Jimenez et al. |
| 2012/0275845 A1 | 11/2012 | Etling |
| 2012/0275860 A1 | 11/2012 | Exline |
| 2012/0275861 A1 | 11/2012 | Myslowski et al. |
| 2012/0275862 A1 | 11/2012 | Vitale |
| 2012/0275881 A1 | 11/2012 | Mueller |
| 2012/0275913 A1 | 11/2012 | Robertson, Jr. et al. |
| 2012/0275924 A1 | 11/2012 | Perkinson |
| 2012/0275927 A1 | 11/2012 | Rhim |
| 2012/0275970 A1 | 11/2012 | Nash et al. |
| 2012/0275999 A1 | 11/2012 | Bell et al. |
| 2012/0276005 A1 | 11/2012 | Yang et al. |
| 2012/0276008 A1 | 11/2012 | Walkenhorst et al. |
| 2012/0276009 A1 | 11/2012 | Pfeifer et al. |
| 2012/0276011 A1 | 11/2012 | Kupussamy et al. |
| 2012/0276021 A1 | 11/2012 | Kumar et al. |
| 2012/0276025 A1 | 11/2012 | Florence et al. |
| 2012/0276041 A1 | 11/2012 | Salamone et al. |
| 2012/0276053 A1 | 11/2012 | Kirn |
| 2012/0276061 A1 | 11/2012 | Grazia et al. |
| 2012/0276062 A1 | 11/2012 | Kellar et al. |
| 2012/0276064 A1 | 11/2012 | Blau et al. |
| 2012/0276067 A1 | 11/2012 | Westenfelder |
| 2012/0276068 A1 | 11/2012 | Sabaawy |
| 2012/0276069 A1 | 11/2012 | Karperien et al. |
| 2012/0276071 A1 | 11/2012 | Fraser, Jr. |
| 2012/0276073 A1 | 11/2012 | Schachner et al. |
| 2012/0276074 A1 | 11/2012 | Scharenberg et al. |
| 2012/0276080 A1 | 11/2012 | Kinoshita et al. |
| 2012/0276084 A1 | 11/2012 | Schaumberg et al. |
| 2012/0276087 A1 | 11/2012 | Schafer et al. |
| 2012/0276088 A1 | 11/2012 | El-Deiry et al. |
| 2012/0276089 A1 | 11/2012 | Lee et al. |
| 2012/0276101 A1 | 11/2012 | Kwak et al. |
| 2012/0276103 A1 | 11/2012 | Karperien et al. |
| 2012/0276104 A1 | 11/2012 | Woisetschlager |
| 2012/0276110 A1 | 11/2012 | Simard |
| 2012/0276111 A1 | 11/2012 | Hafezi-Moghadam |
| 2012/0276126 A1 | 11/2012 | Varadhachary et al. |
| 2012/0276130 A1 | 11/2012 | Margarit Y Ros et al. |
| 2012/0276139 A1 | 11/2012 | Moormann et al. |
| 2012/0276143 A1 | 11/2012 | O'Mahony et al. |
| 2012/0276144 A1 | 11/2012 | Kernodle et al. |
| 2012/0276149 A1 | 11/2012 | Littman et al. |
| 2012/0276150 A1 | 11/2012 | Lauritzen et al. |
| 2012/0276151 A1 | 11/2012 | Lewis et al. |
| 2012/0276152 A1 | 11/2012 | Hossainy et al. |
| 2012/0276161 A1 | 11/2012 | Gravagna et al. |
| 2012/0276164 A1 | 11/2012 | Tuominen et al. |
| 2012/0276169 A1 | 11/2012 | Kang et al. |
| 2012/0276173 A1 | 11/2012 | Marcum et al. |
| 2012/0276182 A1 | 11/2012 | Baker, Jr. et al. |
| 2012/0276185 A1 | 11/2012 | Hossainy et al. |
| 2012/0276188 A1 | 11/2012 | Barrows |
| 2012/0276189 A1 | 11/2012 | Johnson |
| 2012/0276193 A1 | 11/2012 | Graversen et al. |
| 2012/0276201 A1 | 11/2012 | Trachtman |
| 2012/0276202 A1 | 11/2012 | Selim et al. |
| 2012/0276203 A1 | 11/2012 | Selim et al. |
| 2012/0276204 A1 | 11/2012 | Remington et al. |
| 2012/0276213 A1 | 11/2012 | Chen |
| 2012/0276218 A1 | 11/2012 | Jung et al. |
| 2012/0276232 A1 | 11/2012 | Marczyk et al. |
| 2012/0276237 A1 | 11/2012 | Heymanns et al. |
| 2012/0276278 A1 | 11/2012 | Qiu et al. |
| 2012/0276286 A1 | 11/2012 | Vijayakumar |
| 2012/0276296 A1 | 11/2012 | Fieberg et al. |
| 2012/0276297 A1 | 11/2012 | Cypcar et al. |
| 2012/0276304 A1 | 11/2012 | Derrien |
| 2012/0276330 A1 | 11/2012 | Durney et al. |
| 2012/0276365 A1 | 11/2012 | Petuskey et al. |
| 2012/0276375 A1 | 11/2012 | Colgan et al. |

(56) References Cited

U.S. PATENT DOCUMENTS

| | | |
|---|---|---|
| 2012/0276381 A1 | 11/2012 | Cypcar |
| 2012/0276427 A1 | 11/2012 | Kim |
| 2012/0276463 A1 | 11/2012 | Grannell et al. |
| 2012/0276465 A1 | 11/2012 | Paganelli |
| 2012/0276469 A1 | 11/2012 | Shizuku |
| 2012/0276509 A1 | 11/2012 | Iannotti et al. |
| 2012/0276518 A1 | 11/2012 | Gillis |
| 2012/0276522 A1 | 11/2012 | Huang et al. |
| 2012/0276528 A1 | 11/2012 | Cargill et al. |
| 2012/0276529 A1 | 11/2012 | Galisson et al. |
| 2012/0276537 A1 | 11/2012 | Kühn et al. |
| 2012/0276552 A1 | 11/2012 | Lu |
| 2012/0276553 A1 | 11/2012 | Gronthos et al. |
| 2012/0276554 A1 | 11/2012 | Gutteridge et al. |
| 2012/0276555 A1 | 11/2012 | Kuhn et al. |
| 2012/0276558 A1 | 11/2012 | Soper et al. |
| 2012/0276572 A1 | 11/2012 | Shekdar et al. |
| 2012/0276581 A1 | 11/2012 | Arav et al. |
| 2012/0276588 A1 | 11/2012 | Hallen-Adams et al. |
| 2012/0276591 A1 | 11/2012 | Kneissel et al. |
| 2012/0276618 A1 | 11/2012 | Dayton et al. |
| 2012/0276626 A1 | 11/2012 | Shogbon et al. |
| 2012/0276627 A1 | 11/2012 | Kelnar et al. |
| 2012/0276628 A1 | 11/2012 | Khan et al. |
| 2012/0276632 A1 | 11/2012 | Strunk et al. |
| 2012/0276679 A1 | 11/2012 | Wu |
| 2012/0276694 A1 | 11/2012 | Koezuka et al. |
| 2012/0276754 A1 | 11/2012 | Cordingley et al. |
| 2012/0276887 A1 | 11/2012 | Romine et al. |
| 2012/0276928 A1 | 11/2012 | Shutter |
| 2012/0277006 A1 | 11/2012 | Kim |
| 2012/0277008 A1 | 11/2012 | Kitchen et al. |
| 2012/0277051 A1 | 11/2012 | Cooper et al. |
| 2012/0277073 A1 | 11/2012 | Bartsch |
| 2012/0277093 A1 | 11/2012 | Andrew et al. |
| 2012/0277110 A1 | 11/2012 | Andre et al. |
| 2012/0277111 A1 | 11/2012 | Crabtree et al. |
| 2012/0277112 A1 | 11/2012 | Linn et al. |
| 2012/0277118 A1 | 11/2012 | Bhati et al. |
| 2012/0277120 A1 | 11/2012 | Serber et al. |
| 2012/0277144 A1 | 11/2012 | Duckers |
| 2012/0277152 A1 | 11/2012 | Ringeisen et al. |
| 2012/0277155 A1 | 11/2012 | VanAntwerp et al. |
| 2012/0277156 A1 | 11/2012 | Gross et al. |
| 2012/0277157 A1 | 11/2012 | Hillman |
| 2012/0277161 A1 | 11/2012 | Agrez et al. |
| 2012/0277162 A1 | 11/2012 | Krasnoperov et al. |
| 2012/0277173 A1 | 11/2012 | Eidenberger |
| 2012/0277179 A1 | 11/2012 | Bhargava |
| 2012/0277195 A1 | 11/2012 | Banov et al. |
| 2012/0277203 A1 | 11/2012 | Lasley et al. |
| 2012/0277204 A1 | 11/2012 | Taniguchi et al. |
| 2012/0277205 A1 | 11/2012 | Badorc et al. |
| 2012/0277210 A1 | 11/2012 | Catron et al. |
| 2012/0277215 A1 | 11/2012 | Ksander et al. |
| 2012/0277228 A1 | 11/2012 | Sutton et al. |
| 2012/0277229 A1 | 11/2012 | Bearss et al. |
| 2012/0277251 A1 | 11/2012 | Palladino et al. |
| 2012/0277265 A1 | 11/2012 | Deraeve et al. |
| 2012/0277269 A1 | 11/2012 | Reilly |
| 2012/0277271 A1 | 11/2012 | Nadeson et al. |
| 2012/0277277 A1 | 11/2012 | Wallace et al. |
| 2012/0277279 A1 | 11/2012 | Barnett et al. |
| 2012/0277282 A1 | 11/2012 | Gotthardt et al. |
| 2012/0277288 A1 | 11/2012 | Drumm et al. |
| 2012/0277307 A1 | 11/2012 | Waddell |
| 2012/0277309 A1 | 11/2012 | Severa et al. |
| 2012/0277312 A1 | 11/2012 | Mink et al. |
| 2012/0277316 A1 | 11/2012 | Tillman et al. |
| 2012/0277319 A1 | 11/2012 | Steigerwald et al. |
| 2012/0277324 A1 | 11/2012 | Burk et al. |
| 2012/0277364 A1 | 11/2012 | Lolli et al. |
| 2012/0277376 A1 | 11/2012 | Baker, Jr. et al. |
| 2012/0277382 A1 | 11/2012 | Booth et al. |
| 2012/0277412 A1 | 11/2012 | Furusako et al. |
| 2012/0277430 A1 | 11/2012 | Taniguchi et al. |
| 2012/0277431 A1 | 11/2012 | Taniguchi et al. |
| 2012/0277451 A1 | 11/2012 | Ochiai |
| 2012/0277453 A1 | 11/2012 | Franklin et al. |
| 2012/0277517 A1 | 11/2012 | Ivkov et al. |
| 2012/0277521 A1 | 11/2012 | Chamberlin |
| 2012/0277522 A1 | 11/2012 | Shalon et al. |
| 2012/0277523 A1 | 11/2012 | Shalon et al. |
| 2012/0277537 A1 | 11/2012 | Kucklick et al. |
| 2012/0277544 A1 | 11/2012 | Fernandes et al. |
| 2012/0277546 A1 | 11/2012 | Soykan et al. |
| 2012/0277567 A1 | 11/2012 | Harlev et al. |
| 2012/0277572 A1 | 11/2012 | Hubbard |
| 2012/0277574 A1 | 11/2012 | Panescu |
| 2012/0277576 A1 | 11/2012 | Lui |
| 2012/0277578 A1 | 11/2012 | Gunday et al. |
| 2012/0277582 A1 | 11/2012 | Mafi |
| 2012/0277584 A1 | 11/2012 | Tanaka et al. |
| 2012/0277592 A1 | 11/2012 | Zelenka et al. |
| 2012/0277599 A1 | 11/2012 | Greenhut |
| 2012/0277600 A1 | 11/2012 | Greenhut |
| 2012/0277618 A1 | 11/2012 | Giftakis et al. |
| 2012/0277621 A1 | 11/2012 | Gerber et al. |
| 2012/0277624 A1 | 11/2012 | Cucin |
| 2012/0277626 A1 | 11/2012 | Burbank et al. |
| 2012/0277638 A1 | 11/2012 | Skelton et al. |
| 2012/0277639 A1 | 11/2012 | Pollock et al. |
| 2012/0277642 A1 | 11/2012 | Smith et al. |
| 2012/0277668 A1 | 11/2012 | Chawla |
| 2012/0277671 A1 | 11/2012 | Fuentes |
| 2012/0277672 A1 | 11/2012 | Pepper et al. |
| 2012/0277674 A1 | 11/2012 | Clark, III et al. |
| 2012/0277693 A1 | 11/2012 | Bailey |
| 2012/0277716 A1 | 11/2012 | Ali et al. |
| 2012/0277718 A1 | 11/2012 | Campbell et al. |
| 2012/0277720 A1 | 11/2012 | Humes et al. |
| 2012/0277725 A1 | 11/2012 | Kassab et al. |
| 2012/0277729 A1 | 11/2012 | Melsheimer |
| 2012/0277730 A1 | 11/2012 | Salahieh et al. |
| 2012/0277736 A1 | 11/2012 | Francischelli |
| 2012/0277740 A1 | 11/2012 | Warnking et al. |
| 2012/0277741 A1 | 11/2012 | Davalos et al. |
| 2012/0277743 A1 | 11/2012 | Vallittu |
| 2012/0277746 A1 | 11/2012 | Morgan et al. |
| 2012/0277749 A1 | 11/2012 | Mootien et al. |
| 2012/0277752 A1 | 11/2012 | Wasielewski |
| 2012/0277753 A1 | 11/2012 | Linderman et al. |
| 2012/0277756 A1 | 11/2012 | Ray et al. |
| 2012/0277766 A1 | 11/2012 | Ferree |
| 2012/0277770 A1 | 11/2012 | Fenton et al. |
| 2012/0277771 A1 | 11/2012 | Vaz et al. |
| 2012/0277772 A1 | 11/2012 | Aben et al. |
| 2012/0277773 A1 | 11/2012 | Sargeant et al. |
| 2012/0277774 A1 | 11/2012 | Guo |
| 2012/0277776 A1 | 11/2012 | Kraemer et al. |
| 2012/0277781 A1 | 11/2012 | Gertner |
| 2012/0277784 A1 | 11/2012 | Berez et al. |
| 2012/0277785 A1 | 11/2012 | Aggerholm et al. |
| 2012/0277786 A1 | 11/2012 | Mohl |
| 2012/0277791 A1 | 11/2012 | Abo-Auda et al. |
| 2012/0277792 A1 | 11/2012 | Teeslink et al. |
| 2012/0277793 A1 | 11/2012 | Marczyk et al. |
| 2012/0277798 A1 | 11/2012 | Benson et al. |
| 2012/0277800 A1 | 11/2012 | Jackson |
| 2012/0277807 A1 | 11/2012 | Myung et al. |
| 2012/0277811 A1 | 11/2012 | Lauchner et al. |
| 2012/0277812 A1 | 11/2012 | Kraus |
| 2012/0277814 A1 | 11/2012 | Schuler |
| 2012/0277820 A1 | 11/2012 | Wu et al. |
| 2012/0277823 A1 | 11/2012 | Gerber et al. |
| 2012/0277825 A1 | 11/2012 | Mawson et al. |
| 2012/0277833 A1 | 11/2012 | Gerber et al. |
| 2012/0277835 A1 | 11/2012 | Della Santina et al. |
| 2012/0277837 A1 | 11/2012 | Schuler |
| 2012/0277843 A1 | 11/2012 | Weber et al. |
| 2012/0277845 A1 | 11/2012 | Bowe |
| 2012/0277846 A1 | 11/2012 | Schreck et al. |
| 2012/0277852 A1 | 11/2012 | Shukla et al. |
| 2012/0277853 A1 | 11/2012 | Rothstein |

(56) References Cited

U.S. PATENT DOCUMENTS

| | | |
|---|---|---|
| 2012/0277854 A1 | 11/2012 | Ryan |
| 2012/0277855 A1 | 11/2012 | Lashinski et al. |
| 2012/0277856 A1 | 11/2012 | Spenser et al. |
| 2012/0277862 A1 | 11/2012 | Tornier et al. |
| 2012/0277864 A1 | 11/2012 | Brodke et al. |
| 2012/0277865 A1 | 11/2012 | Trieu et al. |
| 2012/0277867 A1 | 11/2012 | Kana et al. |
| 2012/0277872 A1 | 11/2012 | Kana et al. |
| 2012/0277873 A1 | 11/2012 | Kana et al. |
| 2012/0277879 A1 | 11/2012 | Ripamonti |
| 2012/0277880 A1 | 11/2012 | Winslow et al. |
| 2012/0277882 A1 | 11/2012 | Huang et al. |
| 2012/0277896 A1 | 11/2012 | Uekita et al. |
| 2012/0277903 A1 | 11/2012 | Schaefer |
| 2012/0277939 A1 | 11/2012 | Kumar |
| 2012/0277940 A1 | 11/2012 | Kumar et al. |
| 2012/0277949 A1 | 11/2012 | Ghimire et al. |
| 2012/0277979 A1 | 11/2012 | Kato et al. |
| 2012/0277998 A1 | 11/2012 | Bevilacqua et al. |
| 2012/0277999 A1 | 11/2012 | Somogyi et al. |
| 2012/0278032 A1 | 11/2012 | Chen |
| 2012/0278098 A1 | 11/2012 | Vovan et al. |
| 2012/0278099 A1 | 11/2012 | Kelly et al. |
| 2012/0278123 A1 | 11/2012 | Houle |
| 2012/0278144 A1 | 11/2012 | Popilock et al. |
| 2012/0278195 A1 | 11/2012 | Joseph |
| 2012/0278200 A1 | 11/2012 | van Coppenolle et al. |
| 2012/0278242 A1 | 11/2012 | Griffith |
| 2012/0278411 A1 | 11/2012 | Lavine |
| 2012/0278439 A1 | 11/2012 | Ahiska et al. |
| 2012/0278454 A1 | 11/2012 | Stewart et al. |
| 2012/0278484 A1 | 11/2012 | Westphal |
| 2012/0278520 A1 | 11/2012 | Barrenscheen et al. |
| 2012/0278554 A1 | 11/2012 | Eilert |
| 2012/0278592 A1 | 11/2012 | Tran |
| 2012/0278597 A1 | 11/2012 | De Atley et al. |
| 2012/0278654 A1 | 11/2012 | Shen et al. |
| 2012/0278657 A1 | 11/2012 | Baker et al. |
| 2012/0278676 A1 | 11/2012 | Teraura |
| 2012/0278684 A1 | 11/2012 | Eldredge et al. |
| 2012/0278689 A1 | 11/2012 | Tamo et al. |
| 2012/0278760 A1 | 11/2012 | Cerny et al. |
| 2012/0278771 A1 | 11/2012 | Ren |
| 2012/0278799 A1 | 11/2012 | Starks et al. |
| 2012/0278865 A1 | 11/2012 | Sawdy |
| 2012/0278913 A1 | 11/2012 | Fraser |
| 2012/0278947 A1 | 11/2012 | Guo et al. |
| 2012/0278957 A1 | 11/2012 | Phan et al. |
| 2012/0283520 A1 | 11/2012 | Kleyman |
| 2012/0283758 A1 | 11/2012 | Miller |
| 2013/0041395 A1 | 2/2013 | De Canniere |
| 2013/0066275 A1 | 3/2013 | de Canniere |
| 2013/0090684 A1 | 4/2013 | Van Bladel et al. |
| 2014/0088417 A1 | 3/2014 | Alhumaid |
| 2014/0100604 A1 | 4/2014 | Litvack et al. |
| 2014/0142687 A1 | 5/2014 | Canniere et al. |
| 2014/0142689 A1 | 5/2014 | de Canniere et al. |
| 2014/0172004 A1 | 6/2014 | Canniere |
| 2014/0172005 A1 | 6/2014 | Canniere |
| 2015/0025312 A1 | 1/2015 | Canniere |
| 2015/0148590 A1 | 5/2015 | Canniere |

FOREIGN PATENT DOCUMENTS

| | | |
|---|---|---|
| EP | 1169968 | 1/2002 |
| EP | 1222896 | 7/2002 |
| EP | 1266626 | 12/2002 |
| EP | 1269919 | 1/2003 |
| EP | 1254634 | 7/2003 |
| EP | 1244725 | 7/2005 |
| EP | 1773239 B1 | 3/2010 |
| EP | 2 363 075 A1 | 9/2011 |
| JP | 2012-200597 A | 10/2012 |
| JP | 2013-523408 A | 6/2013 |
| JP | 2013-536036 A | 9/2013 |
| WO | WO 96/32882 A1 | 10/1996 |
| WO | WO 02/069783 A2 | 9/2002 |
| WO | WO 2009/045265 A1 | 4/2009 |
| WO | WO 2009/137755 A2 | 11/2009 |
| WO | WO 2011/130456 A1 | 10/2011 |
| WO | WO 2011/163666 A1 | 12/2011 |
| WO | WO 2012/025927 A2 | 3/2012 |
| WO | WO 2012 040865 | 4/2012 |
| WO | WO2012040865 A1 | 4/2012 |
| WO | WO 2012/106398 A1 | 8/2012 |
| WO | WO2012016398 A1 | 9/2012 |
| WO | WO2013/023016 | 2/2013 |
| WO | WO 2013036742 | 3/2013 |
| WO | WO2015081053 A1 | 6/2015 |

OTHER PUBLICATIONS

PCT/US2012/050066, dated Oct. 26, 2012, International Search Report and Written Opinion.
PCT/US2012/050066, dated Feb. 20, 2014, International Preliminary Report on Patentability.
PCT/US2013/070254, dated Mar. 28, 2014, International Search Report and Written Opinion.
PCT/US2013/070254, dated Jun. 25, 2015, International Preliminary Report on Patentability.
PCT/US2014/062856, dated Jan. 28, 2015, International Search Report and Written Opinion.
PCT/US2014/062856, dated May 12, 2016, International Preliminary Report on Patentability.
PCT/US2015/012426, dated May 5, 2015, International Search Report and Written Opinion.
PCT/US2015/012426, dated Aug. 18, 2016, International Preliminary Report on Patentability.
EP 13862921.7, dated Jun. 30, 2016, Extended European Search Report.
EP 14857755.4, dated Jun. 23, 2017, Extended European Search Report.
EP 15746528.7, dated Aug. 17, 2017, Extended European Search Report.
Australian Examination Report dated Jul. 23, 2018 for Application No. AU 2014342390.
Canadian Office Communication dated Mar. 8, 2018 for Application No. CA 2,938,000.
English translation of Japanese Office Action dated Jul. 25, 2017 for Application No. JP 2016-550499.
Mexican Office Action dated Jan. 22, 2016 for Application No. MX/a/2014/001480.
International Search Report and Written Opinion dated Oct. 26, 2012 in connection with International Application No. PCT/US2012/050066.
International Preliminary Report on Patentability dated Feb. 20, 2014 in connection with International Application No. PCT/US2012/050066.
International Search Report and Written Opinion dated Mar. 28, 2014 in connection with International Application No. PCT/US2013/070254.
International Preliminary Report on Patentability dated Jun. 25, 2015 in connection with International Application No. PCT/US2013/070254.
International Search Report and Written Opinion dated Jan. 28, 2015 in connection with International Application No. PCT/US2014/062856.
International Preliminary Report on Patentability dated May 12, 2016 in connection with International Application No. PCT/US2014/062856.
International Search Report and Written Opinion dated May 5, 2015 for corresponding International Application No. PCT/US2015/012426.
International Preliminary Report on Patentability dated Aug. 18, 2016 for corresponding International Application No. PCT/US2015/012426.
Extended European Search Report dated Jun. 30, 2016 in connection with European Application No. 13862921.7.

(56) References Cited

OTHER PUBLICATIONS

Extended European Search Report dated Jun. 23, 2017 in connection with European Application No. 14857755.4.
Extended European Search Report dated Aug. 17, 2017 in connection with European Application No. 15746528.7.
Australian Examination Report dated Jul. 23, 2018 in connection with Australian Application No. 2014342390.
Canadian Office Communication dated Mar. 8, 2018 in connection with Canadian Application No. 2,938,000.
English translation of Japanese Office Action dated Jul. 25, 2017 in connection with Japanese Application No. 2016-550499.
Mexican Office Action dated Jan. 22, 2016 in connection with Mexican Application No. MX/a/2014/001480.

* cited by examiner

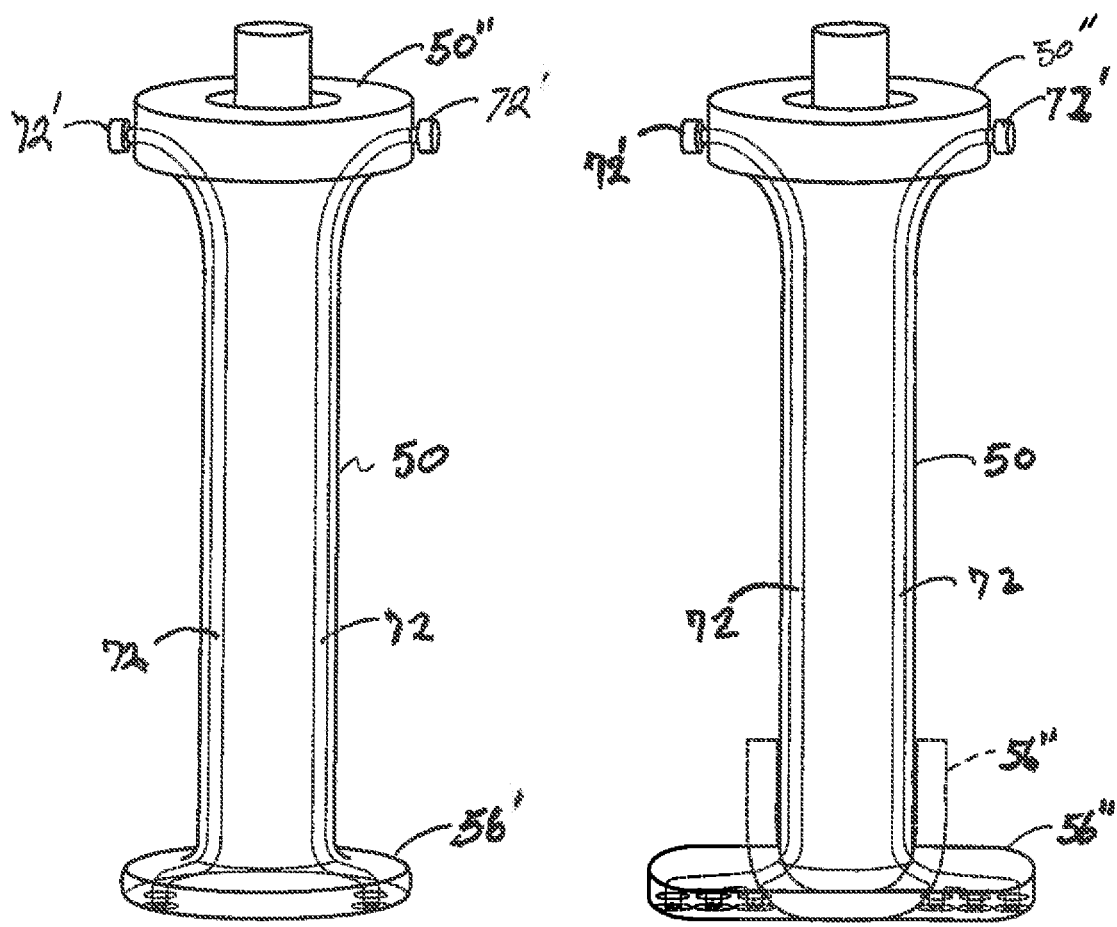
FIG. 7A    FIG. 8A
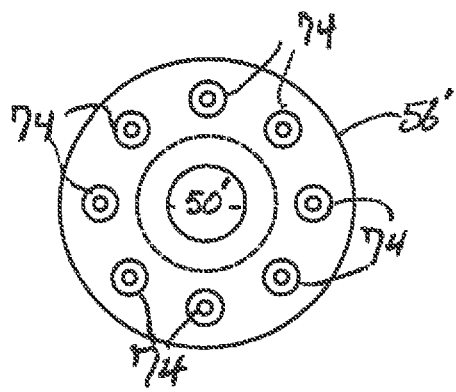 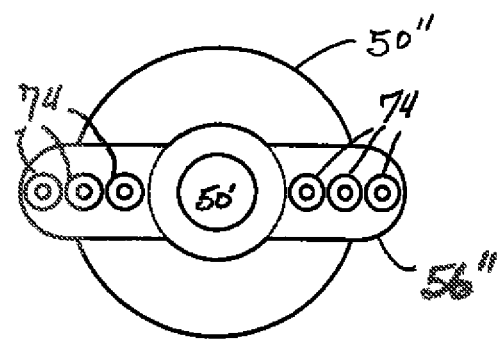
FIG. 7B    FIG. 8B

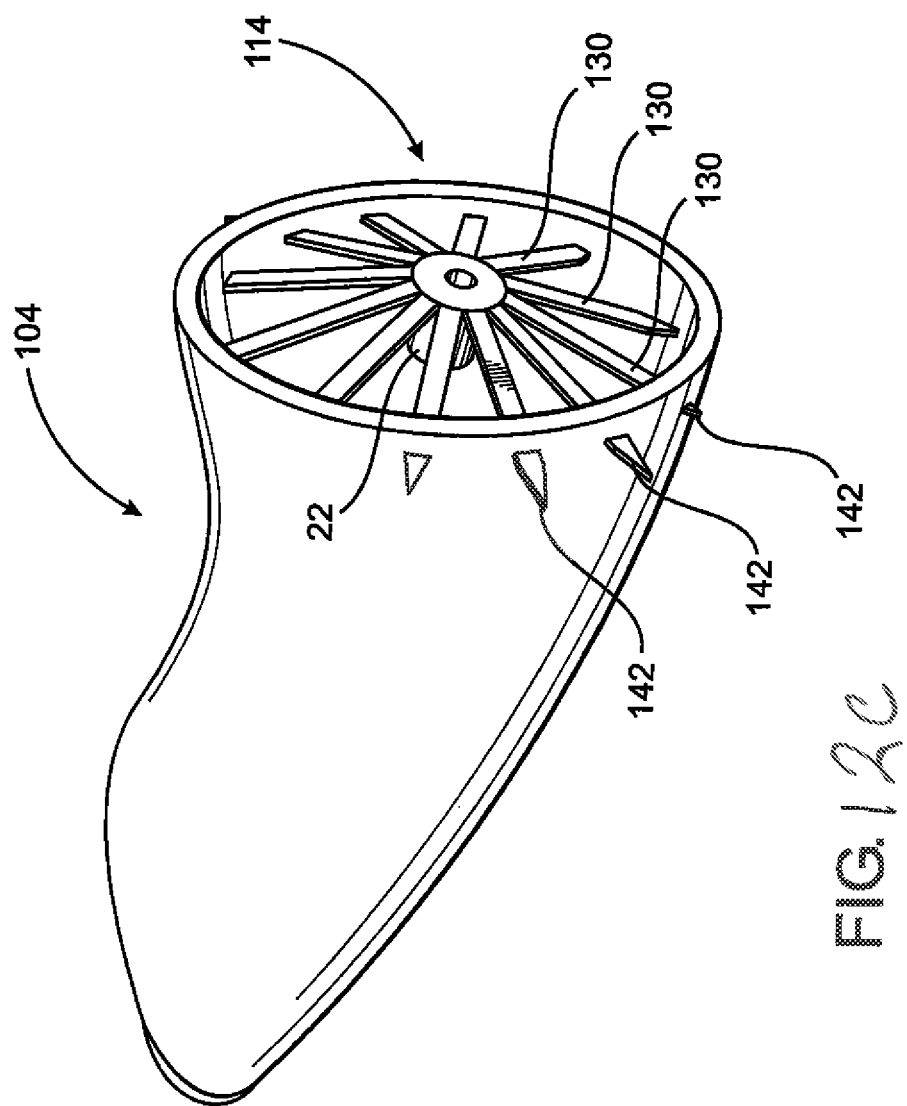

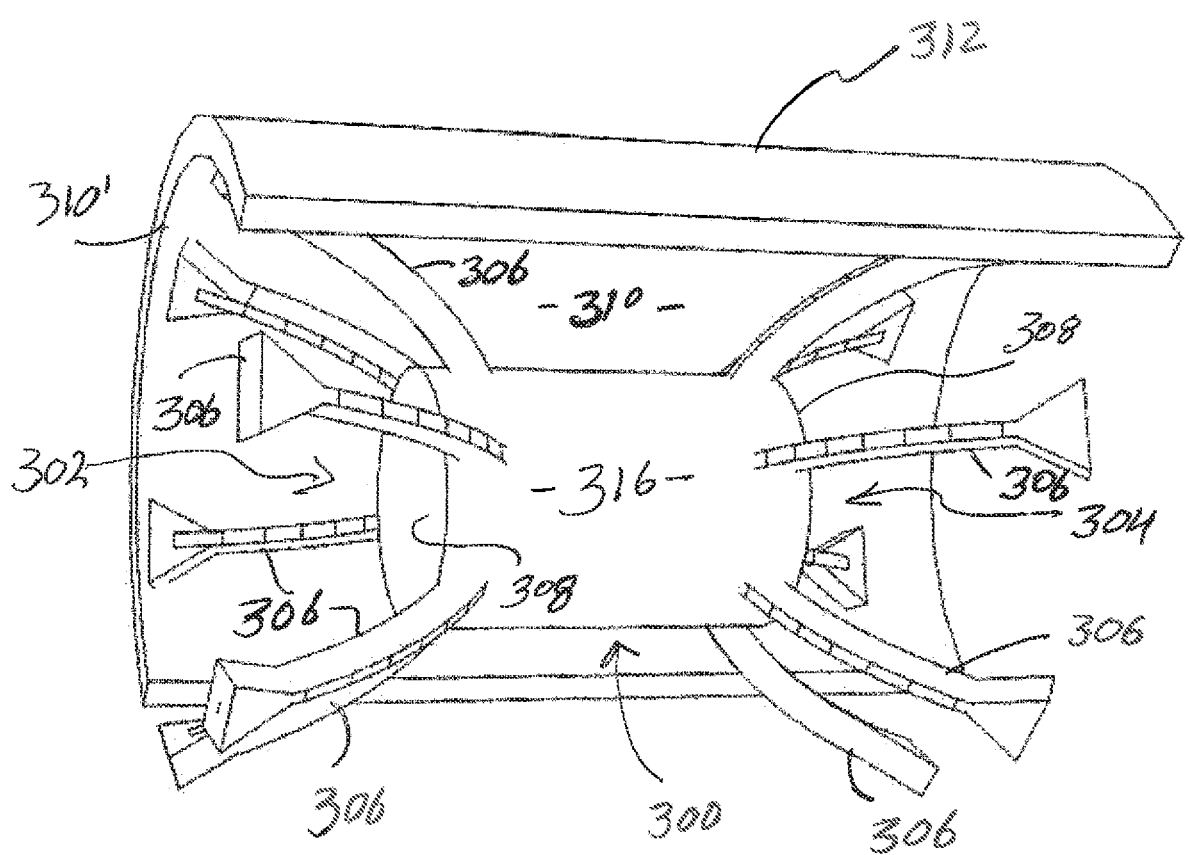

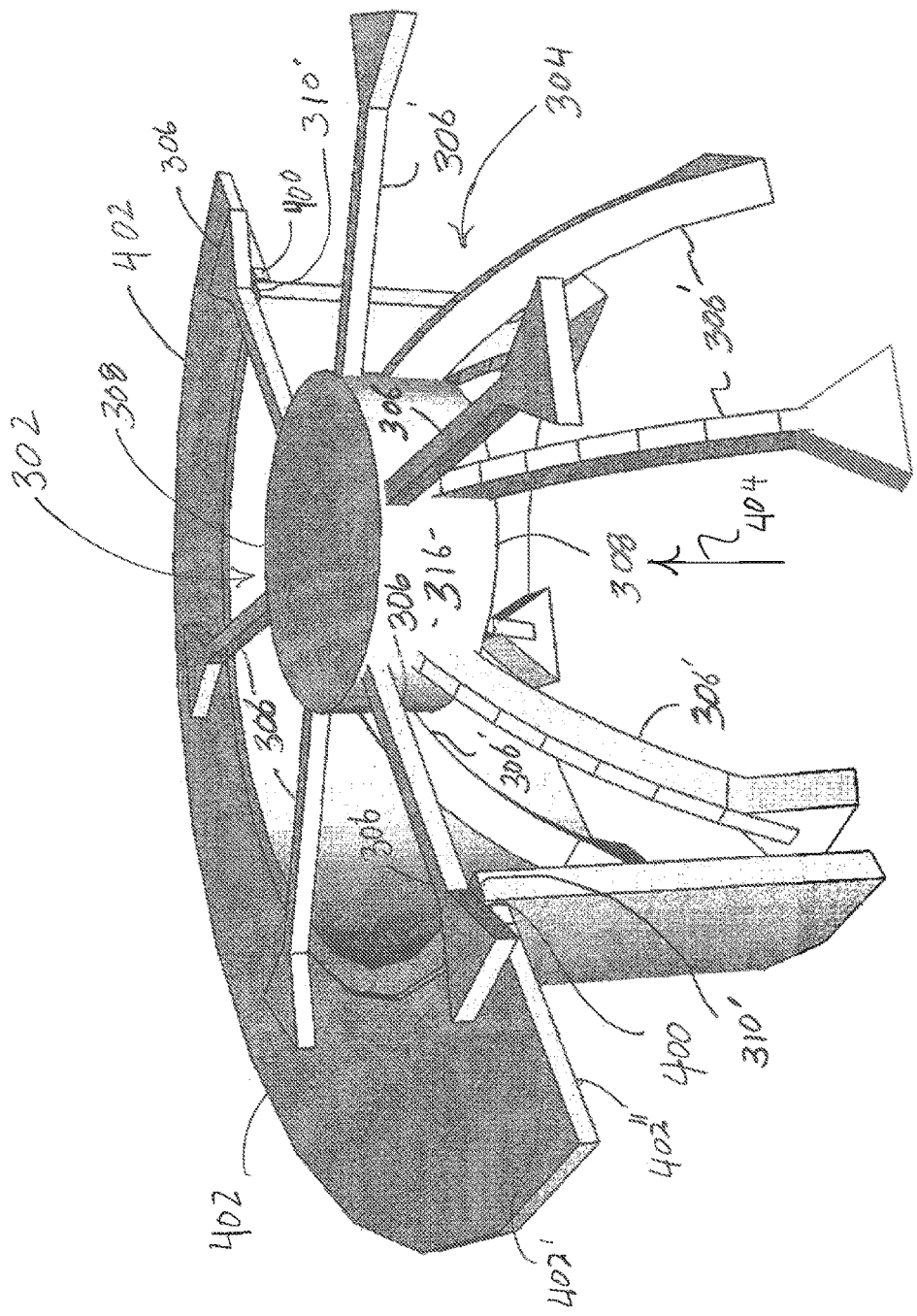

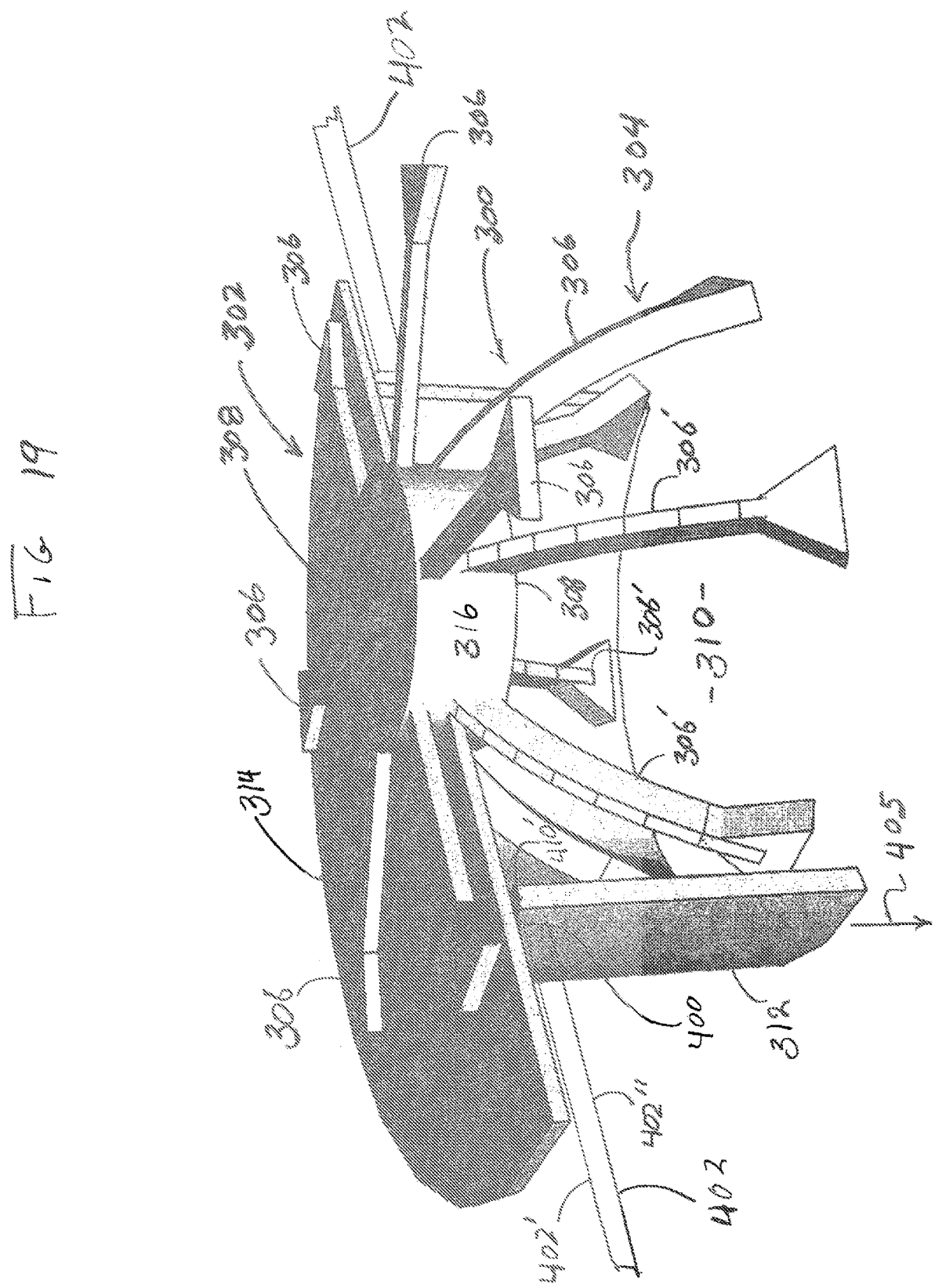

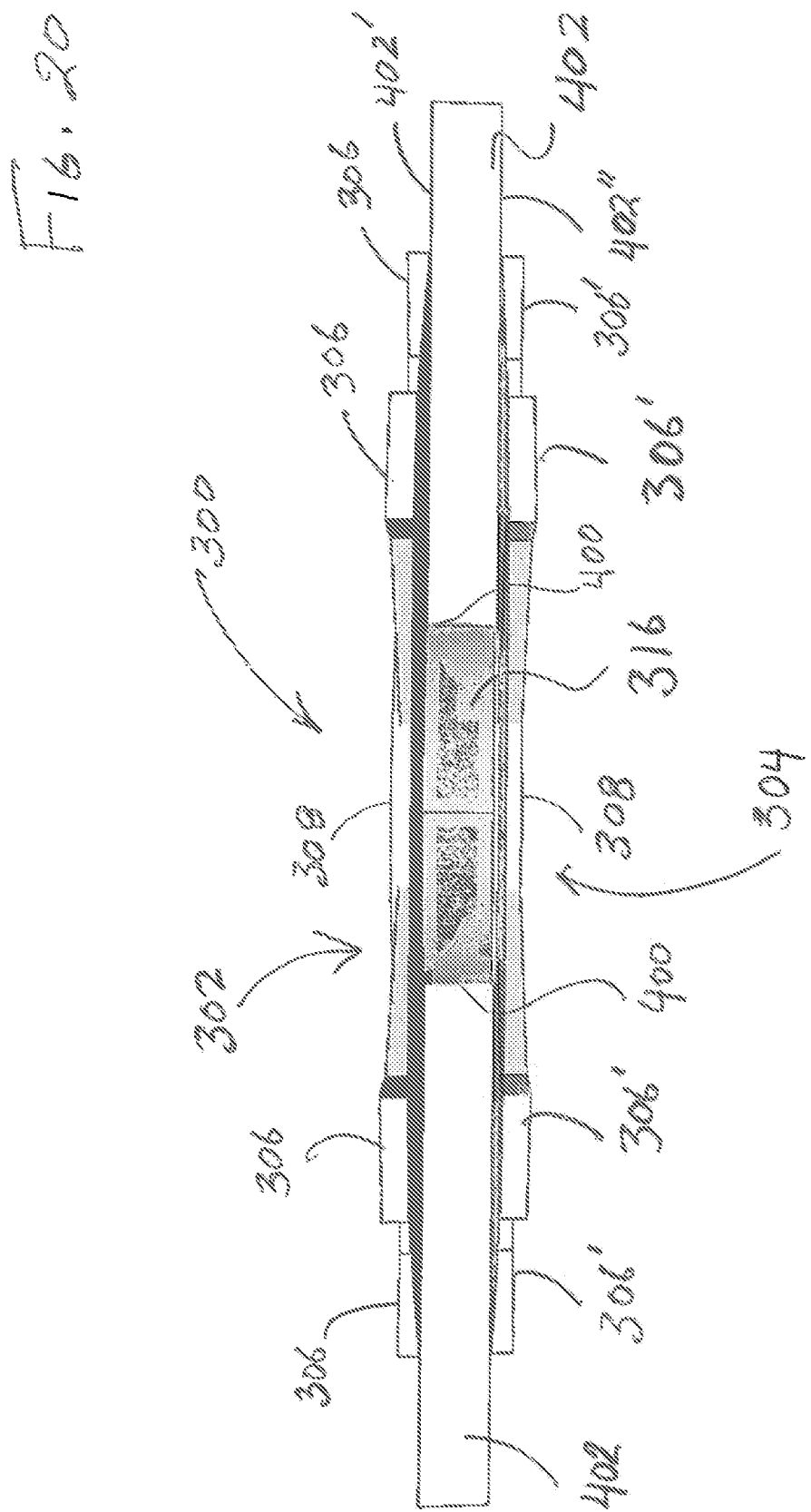

CLOSURE SYSTEM FOR ATRIAL WALL

CLAIM OF PRIORITY

The present application is a continuation-in-part of U.S. application Ser. No. 13/570,347, filed on Aug. 9, 2012, which is a continuation-in-part of U.S. application Ser. No. 13/442,230, filed on Apr. 9, 2012, which claims the benefit of priority to U.S. Provisional Application No. 61/574,798, filed on Aug. 9, 2011, and wherein all of the above are incorporated herein in their entirety by reference. The present application is also a continuation-in-part of U.S. application Ser. No. 13/838,199, filed on Mar. 15, 2013, which is a continuation-in-part of U.S. application Ser. No. 13/714,989, filed on Dec. 14, 2012, all of which are included herein in their entirety by reference.

BACKGROUND OF THE INVENTION

Field of the Invention

The invention relates to intracardiac surgical procedures and more specifically to an assembly and method for introducing medical instrumentation through one or more introductory sheaths, to a predetermined intracardiac depth, into a selected one of the left atrium or right atrium through a thoracic passage and correspondingly disposed intercostal spaces. Upon completion of the required surgical procedure on the interior of the targeted atrium, a closure assembly is disposed in closing relation to the entry site of the instrumentation and introductory sheath in the pericardium and targeted atrium wall.

Description of the Related Art

When the heart or any of its component parts develops a defect or disease, intracardiac intervention is often necessary to correct, repair, and/or replace damaged or defected cardiac components. Classically, this has been accomplished through surgery in which the chest of the patient is opened and the heart, which is arrested and/or bypassed, is operated on. This can be a very dangerous procedure replete with many possible complications resulting from, at the very least, stopping or bypassing the heart, general anesthesia administered during the procedure, risk of infection from a large opening in the chest cavity, and scarring. Moreover, surgery is not a viable option for many elderly and/or frail patients who are at an increased risk for these complications.

A widely used alternative to cardiac surgery is invasive cardiology, in which catheters are introduced into blood vessels at remote, or peripheral, sites from the heart and are steered through veins and arteries of the body to reach the heart. For example, the femoral vessels, radial artery, subclavian artery and the jugular veins can be used for insertion of catheters for remote cardiac intervention. While this approach avoids many of the risks of surgery, it suffers from significant technical limitations. First, the anatomy and size of the peripheral vessels precludes the use of some catheters. For example, the capillaries and some veins are too narrow to accommodate catheters. Some veins may not be sufficiently sized for a larger catheter, such as in excess of 12 French, or to accept a plurality of catheters simultaneously. The suitability of blood vessels for remote cardiac access may be further exacerbated in many patients, namely the elderly, in which the vessels are narrowed, calcified or tortuous, making access to the heart difficult or impossible. Moreover, the branched network of blood vessels makes the usage of multiple catheters limited to only those catheters having a small caliber. However, even in situations such as these, maneuverability is limited since very little torque can be developed between two catheters threaded through a common blood vessel once inside the heart to address any target structure. This can involve severe limitations since many intracardiac maneuvers require complex access and steering such as, but not limited to, trans-septal punctures, steering the catheter through the inter-atrial septum to access the mitral valve, such as for delivering a MITRACLIP®, percutaneous mitral dilatation, and steering ablation catheters around the openings of the pulmonary veins.

The distance that separates the entry point of the catheter from the target structure is an additional drawback to invasive cardiac measures performed through blood vessels. Moreover, the further the distance from the remote point of entry to the heart, the further the catheter must be threaded and the greater the risk of inadvertently puncturing the wall of a blood vessel, encountering a blockage or collapsed blood vessel, or other obstacle. Moreover, long catheters are also required when the entry point is remote from the heart, necessitating an increase in materials which can become cumbersome to control and maneuver as intended.

More recently, new approaches to intracardiac structures have been introduced to deliver prostheses, such as aortic valves as in the case of transaortic valve implantation ("TAVI"), for patients who do not qualify for a classical surgical replacement and/or whose peripheral vessels are too small to accommodate the large catheters needed to carry the prosthesis. In such an approach, a direct puncture is made in the apex of the left ventricle of the heart via a small incision in the chest wall by an anterior thoracotomy. This approach is becoming more popular and is currently investigated as a route to deliver treatment for other structural heart disease such as, but not limited to auto-implantable mitral prostheses, etc.

However, this entry procedure also has recognized disadvantages. More specifically, this procedure requires general anesthesia and the indicated thoracotomy generates pain, requires long rehabilitation and in known to result in significant complications in especially frail patients. Further, it involves entering the ventricular wall, which leads to a marginal loss of contractile force of the heart, but also a significant risk of bleeding, since the pressure in the ventricle is about 10 times higher than in the atrium. It also requires passage through the ventricular trabeculae and subvalvular mitral apparatus which are needed to prevent backflow of blood during the contraction of the heart, known as systole.

It would therefore be beneficial to implement an improved and proposed introductory assembly and method of accessing the chambers of the heart and performing intracardiac interventions. Such an improved technique would not require arresting or bypassing the heart and illuminate the blood vessels used for peripheral access to the heart. As a result instrumentation including multiple catheters could be concurrently introduced into predetermined areas of the heart, specifically including the interiors of the right and left atria, in a manner which would eliminate or significantly reduce many of the complications and disadvantages of known surgical procedures.

SUMMARY OF THE INVENTION

The present invention is directed to an introduction assembly and method for accessing intracardiac structures through the insertion of catheters or other instrumentation into either the right or left atrium. At least one puncture or entry site is formed in the targeted atrium of a beating heart, by inserting a lancet through a thoracic passage by way of an appropriate intercostal space and entering the corresponding portion of the pericardial bag surrounding the targeted atrium of the heart. It is recognized, that in some cases, accessing the atrium through the right side of the chest may be preferred. The introductory assembly and method of the present invention can be used and accomplished from any approach to the heart which enables access to the targeted atrium.

Moreover, the present invention may be used with or without lung deflation, although in some situations it may be preferable to deflate one lung, preferably the right lung, to create additional space in which to work. The present invention also has the distinct advantage of allowing a variety of intracardiac maneuvers to be performed. By way of example such intracardiac maneuvers include, but are not limited to, closing para-valvular prosthetic leaks; closing the left atrial appendage; approaching the mitral and/or tricuspid annuli and/or leaflets to deliver devices that restrain their prolapse or limit their dilatation; encircling the pulmonary veins with ablation lines performed with different energy sources, and repair or replacement of a malfunctioning atrio-ventricular valve. Further, the introductory assembly and method may be utilized surgically after a small, possibly robotically-enhanced right thoracotomy. In this case the atria are opened ("atriotomy") to manually perform the intended intracardiac maneuver(s).

Accordingly, the present invention provides many advantages that overcome the limitations of other known ways of accessing and performing intracardiac interventions. Further by way of non-limiting examples, the practicing of the various preferred embodiments of the present invention reduces the limitations imposed by peripheral access to the heart through blood vessels, such as a narrowing of the vascular tree which precluding catheter passage. The present invention facilitates the ability to insert multiple catheters from different entry points through the thoracic wall and into a targeted atrium. This multiple, concurrent insertion capability thereby permits synergistic action, force, and/or torque between the catheters because they need not be coaxially disposed in relation to each other. This is in contrast to catheters inserted through the venous or arterial vasculature.

In addition, the present invention may be practiced under general anesthesia or sedation, advantageously with temporary single lung ventilation and/or intrapleural carbon dioxide$_2$ insufflation to temporarily collapse one lung if additional space is needed. The site of the puncture(s) or entry sites may be predetermined with imaging, such as 3D CT reconstruction of the cardiac structures relative to the rib cage, and may be performed in a cath lab or preferably a hybrid operating room under fluoroscopy, preferably with transoesophageal echographic guidance.

In more specific terms, the present invention includes an introduction assembly for the insertion of medical instruments such as, but not limited to, catheters through a thoracic passage and into either the right or left atrium of the heart. As such, a puncturing or cutting instrument is dimensioned and structured to form an entry site into the targeted right or left atrium by first penetrating a corresponding portion of the pericardial bag. The puncturing instrument is introduced through a thoracic passage and an appropriate intercostal space. In addition, an elongated introductory sheath or like tubular structure includes a central lumen and is movably disposed over the puncturing instrument so as to extend through the entry site formed in both the pericardial bag and the targeted right or left atrium. The sheath also includes a distal end having a predetermined "intracardiac length" which is positioned on the interior of the targeted atrium.

Additional structural features of the inserted introductory sheath include a buffer disposed thereon in segregating relation between the distal end of the sheath, which enters the targeted atrium, and the remainder of the sheath disposed exteriorly of the targeted atrium. As applied, the buffer is disposed in confronting disposition with an exterior portion of the pericardial bag, which corresponds to the entry site. As such, the buffer may be at least partially determinative of the intracardiac length. More specifically, the spacing of the buffer from the extremity of the distal end disposed into the targeted atrium through the entry site may determine the intracardiac length. Therefore, the intracardiac length may be considered the length of the distal end of the sheath which is allowed to pass into the targeted atrium. The central lumen of the introductory sheath is dimensioned and configured to receive and facilitate passage therethrough of instrumentation, such as catheters, which are dedicated to the performance of the intended or predetermined cardiac maneuvers within the targeted atrium. Subsequent to the completion of the intended cardiac maneuvers within the selected atrium, a closure assembly is disposable in an operative position in closing relation to the entry site formed in both the pericardial bag and the atrium wall of the targeted atrium.

Yet another embodiment of the present invention includes additional structure which facilitates the establishment and maintenance of the intended and appropriate intracardiac length of the distal end of the sheath within the targeted atrium, while also preventing the inadvertent removal of the distal end from the targeted atrium. More specifically, one or more preferred embodiments of the present invention include a restricting assembly connected to the distal end of the sheet and movable therewith into and out of the targeted atrium through the entry site. Moreover, the restricting assembly is selectively disposable into a collapsed or reduced size orientation or a restricting orientation. Accordingly, the restricting assembly may be in the form of a collapsible and/or inflatable bladder connected to the distal end and extendable outwardly therefrom when positioned inside the targeted atrium. Further, the dimension and configuration of the bladder, when in the restricting orientation, is sufficient to prevent and/or significantly restrict the removal of the distal end from the interior of the targeted atrium. In contrast, when the expandable or inflatable bladder is in the collapsed orientation it assumes a size and configuration which facilitates or at least allows its passage, along with the distal end, through the entry site into and out of the interior of the targeted atrium. As set forth in greater detail hereinafter, the restricting assembly specifically, but not exclusively, comprising the expandable or inflatable bladder may be used in combination with or independently of the various embodiments of the buffer, as also more specifically described hereinafter. Further, in that the bladder of the restricting assembly is structured to be selectively inflated and deflated, a pressurized fluid source may be connected in fluid communication with the interior of the bladder and facilitate it being inflated and/or deflated as desired. The fluid source may be located exteriorly of the sheath and the thoracic passage and operated independently. Moreover, any of a variety of different fluid communicating connections may be established between the pressurized fluid source and the inflatable bladder.

In one or more preferred embodiments, the buffer comprises or is directly associated with a securing assembly which includes a vacuum or negative pressure source. The buffer is connected to the vacuum source preferably through one or more lumens, flow lines, conduits or other appropriate structures connected to or mounted on the introductory sheath. As such, fluid communication is established between the buffer and the vacuum source to the extent that and appropriate negative pressure is developed and communicated to the buffer through the flow lines. The negative pressure is sufficient to removably secure the buffer to the exterior surface of the pericardial bag in appropriately adjacent relation to the entry site formed in both the pericardial bag and the atrium wall.

Yet additional structural and operative features of at least one preferred embodiment of the buffer include it having an at least partially collapsible construction. Moreover, the collapsible construction of the buffer may comprise a plurality of pads extending outwardly from the exterior of the sheath into a disposition which facilitates the aforementioned removable securement to the exterior of the pericardial bag adjacent to the entry site. In yet another preferred embodiment, the buffer may include an annular configuration connected to and at least partially surrounding exterior portions of the sheath. As such, the buffer is extendable transversely outward from the sheath into the aforementioned removable securement. Therefore, by the application of the negative pressure or vacuum associated with the buffer, the introductory sheath is disposed in movement restricting relative to the entry site. As should be noted, the regulation of fluid flow between the vacuum source and the buffer will allow control over the attachment of detachment of the buffer from its stabilized position relative to the pericardial bag.

Yet additional structural and operative features of at least some of the preferred embodiments of the present invention include the aforementioned closure assembly. More specifically, the closure assembly may comprise a first segment and a second segment respectively and concurrently disposable interiorly and exteriorly of the entry site. As such, the first segment of the closure assembly passes through the lumen of the introductory sheath, through the entry site and into the interior of the targeted atrium. Cooperatively, the second segment of the closure assembly also passes through the lumen of the introductory sheath and is disposed exteriorly of the pericardial wall and entry site. Interconnecting structure between the first and second segments of the closure assembly may be operatively manipulated such as from an exterior of the proximal end of the introductory sheath. Such manipulation of the interconnecting structure will bring the first and second segments to closing relation to the entry site as they are respectively disposed on the interior of the targeted atrium and on the exterior of the pericardial wall. When disposed in the intended sealing relation to the entry site, the first and second segments will effectively "sandwich" the entry site therebetween and facilitate its closure.

The segments of the closure assembly may be formed of a material which will dissolve within the time required for the healing of the entry site. Moreover, the first and second segments of the closure assembly are also formed of a collapsible material which has an at least minimal inherent bias. These collapsible characteristics allow the folding or sufficient size reduction of the first and second segments to pass through the introductory sheath to the entry site. However, upon passage from the open distal end of the lumen of the introductory sheath, each of the first and second segments will be automatically expanded into an intended operative size and configuration for their respective disposition into closing relation to the entry site.

The relative fragile nature of the atrium wall and the possibility of relative displacement or movement between the pericardial bag and the atrium is recognized in the medical arts. Accordingly, additional preferred embodiments of the present invention include at least a portion of sheath being formed of a flexible material. Moreover, the flexible material portion of the sheath should be structured to demonstrate sufficient and/or a predetermined minimum amount of flexibility to accommodate relative movement between the pericardial bag and at least the corresponding wall of the targeted atrium adjacent to the entry site. In addition, this predetermined amount of flexibility should be sufficient to eliminate or significantly reduce the possibility of tearing, ripping or like damage being done to the relatively fragile wall tissue of the targeted atrium. Absent this sufficient flexibility in the distal end, as well as a length of the sheath 50 extending from the distal end and engaging, passing through and/or correspondingly disposed with the entry site, damage of the targeted atrium wall may occur. Such damage may be the result of, but not limited to, forces placed on the atrium wall 44 and/or pericardium bag by a non-flexible portion of the sheath which passes through or is sufficiently close to the entry site and/or which is disposed within the targeted atrium, when relative movement or displacement occurs between the pericardium bag and the atrium wall.

As set forth above, the various preferred embodiments of the present invention are directed not only to the introduction assembly, as generally set forth above, but also to a method of introducing medical instrumentation through a thoracic passage and into a targeted one of the either the right or left atrium of the heart. Accordingly, in cooperation with the introductory assembly as set forth above, the method of at least one preferred embodiment of the present invention comprises the forming of at least one entry site into the targeted atrium and into a corresponding part of the pericardial wall. The aforementioned introductory sheath is positioned such that a distal end thereof, having the predetermined intracardiac length, extends through the thoracic passage and the entry site into the targeted atrium along a predetermined length. Once so positioned, appropriate instrumentation, such as catheters, dedicated to perform the intended predetermined cardiac maneuvers, are passed along the interior of the introductory sheath and into the targeted atrium through the entry site. Once the predetermined cardiac maneuvers have been completed the instrumentation is removed from the selected atrium through the introductory sheath. Thereafter the aforementioned closure assembly is passed through the central lumen of the introductory sheath and into a closing relation with the entry site.

One of the distinct advantages of the present invention is the ability to concurrently insert multiple catheters into the targeted atrium so as to enable the interaction between the concurrently present instruments within the selected atrium. Accordingly, one or more preferred embodiments of the method of the present invention comprises forming a plurality of different entry sites into the targeted atrium and corresponding pericardial wall and positioning different introductory sheaths through the correspondingly positioned ones of a plurality of entry sites. In addition, the corresponding distal ends of the plurality of the introductory sheaths have appropriate intracaridac lengths so as to facilitate the maneuverability and manipulation of the instrumentation once present in the targeted atrium. Upon completion of the required cardiac maneuvers within the selected atrium, a plurality of closure assemblies will pass through different ones of the plurality of introductory sheaths so as to operatively dispose the first and second segments of each of the closure assemblies in closing relation to the formed entry sites, as set forth above.

Yet another preferred embodiment of the present invention is directed to a closure system, apparatus and attendant method for closing and at least partially sealing an opening in the tissue of a patient, such as during a surgical procedure. As indicated herein, surgical procedures specifically directed to the repair of the heart may involve the passage of instrumentation, preferably through an introductory catheter, through the wall of the heart. As such an opening is formed in the heart wall tissue. Upon concluding the surgical procedure, the introductory opening must be closed, sealed, etc. to prevent leakage of blood there through and facilitate proper functioning of the heart.

It is emphasized that while the description of the closure system, apparatus and method of this preferred embodiment of the present invention may be described with specific details to the closing of an opening in the heart wall, the subject closure system can be used for the closing and at least partial sealing of openings in other tissue portions and is not limited to an introductory opening in the heart wall itself.

Accordingly, the closure system of the present invention comprises a first closure member and a second closure member each including a biased construction. The biased construction of the first and second closure members is operative to facilitate disposition thereof into and out of a retracted orientation and an expanded orientation. The first and second closure members are connected in at least partially spaced relation to one another by a connector, which may vary in size, location, structure and material. In addition, the biased construction of the first and second closure members, as well as their interconnection into at least partially spaced relation to one another, facilitates a concurrent disposition of the closure members with one another as they are disposed within the lumen of an introductory instrument towards and into a closing relation to the tissue opening. In addition, the first and second closure members are independently disposed or positioned relative to one another, typically in a successive fashion, into the expanded orientation and a closing relation to the tissue opening, as will be explained in greater detail hereinafter.

Moreover, when the first and second closure members are in the retracted orientation, they are able to move with one another along the interior lumen of the introductory instrument. As the introductory instrument and the internally located closure members approach and at least partially pass through the tissue opening, the first and second closure members independently and successively exit the open end of the lumen of the introductory instrument. As a result, the aforementioned a biased construction of the closure members facilitate their successive disposition into the expanded orientation. At the same time, the introductory instrument will at least initially be disposed through the tissue opening, such that the first closure member will be deployed from the open end of the lumen into the expanded orientation on one side of the tissue opening. Subsequently, the introductory instrument will be withdrawn back through the tissue opening until the open end of the lumen reaches the opposite or "outer" side of the tissue opening. In this location, deployment of the second closure member from the open end of the lumen, into the expanded orientation, will occur. As such, the second closure member will be disposed on the "outer" or opposite side of the tissue opening relative to the first closure member. As a result, the first and second closure members will confront the opposite sides of the tissue opening and thereby be disposed in closing relation to the tissue opening. The structure, dimension and overall configuration of the first and second closure members are such to overlie, cover, close and/or seal the tissue opening as they confront the opposite sides of the tissue in which the tissue opening is formed.

In order to better facilitate a closure and an at least partial sealing of the tissue opening, a cover member or facing is disposed in overlying, covering relation to the base, body or remainder of each of the closure members. The cover member for each closure member is formed of a sufficiently flexible material such as, but not limited to, Dacron, as further described herein. Moreover, the flexibility of the material from which the cover member or cover facing is formed is sufficiently flexible to facilitate its movement with the remainder of the corresponding closure member between the aforementioned retracted an expanded orientations. In cooperation with the cover member or facing member, the biased construction of each or at least one of the first and second closure members comprises a hub or central portion and a plurality of spring-like fingers or ribs. The plurality of fingers or ribs are formed of an inherently biased material which serves to normally bias the plurality of fingers radially outward from the hub or central portion in at least partially spaced relation to one another. It is further emphasized that while at least one preferred embodiment of one or both of the first and second closure members may comprise the plurality of inherently biased fingers or ribs, other structures may be incorporated in one or both the closure members to facilitate and at least partially define the biased construction. However, structural features or components which effectively define the "biased construction" of the first and/or second closure members will be operative to accomplish the aforementioned expanded orientation thereof, as the corresponding ones of the closure members exit the open end of the lumen of the introductory instrument.

In use, the closure system and attendant apparatus comprising the first and second closure members are disposed on the interior of a lumen of a catheter or other appropriate introductory instrument. The first and second closure members, being interconnected in at least partially spaced relation to one another, such as by a connector, will concurrently move within the lumen while in their retracted orientation as the introductory instrument passes through the tissue opening to be closed. Once the open end of the lumen is on the "interior" side or a first side of the tissue opening, the first closure member is deployed from the open end of the lumen, where it will "automatically" assume the aforementioned expanded orientation. Thereafter, the introductory instrument is withdrawn back through the tissue opening and, once disposed outside of the tissue opening, the second closure member will be successively deployed out through the open end of the lumen, and "automatically" assume it's expanded orientation, due to the biased construction thereof.

The dimension and structure of the connector and or interconnection between the first and second closure members is such as to dispose the first and second closure members in confronting relation with opposite sides of the tissue opening. At the same time the connector or interconnection between the first and second closure members is disposed within the tissue opening. The existence of the aforementioned cover member or facing member in overlying, covering relation to corresponding ones of the closure members will serve to effectively close and/or seal opposite ends or sides of the tissue opening. As a result, the tissue opening will be sandwiched between the first and second closure member when in their expanded orientation and closing relation on opposite sides thereof. Upon completion of the first and second closure members being disposed in the closing relation to the tissue opening, as set forth above, the introductory instrument is withdrawn and the first and second closure members are detached from the introductory instrument, while remaining in connected relation to one another.

Accordingly, the present invention overcomes the disadvantages and problems associated with known surgical techniques by implementing the various preferred embodiments of the subject introductory assembly and method for the insertion of instrumentation through a thoracic passage into a selected one of the right or left atrium, as will be described in greater detail hereinafter.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 7A an exterior perspective view of the embodiment of FIGS. 5 and 6.

FIG. 7B is an end view of the embodiment of FIG. 7A.

FIG. 8A is a front perspective view of yet another preferred embodiment similar to but distinguishable from the embodiment of FIGS. 7A and 7B.

FIG. 8B is an end view of the embodiment of FIG. 8A in partial phantom.

FIGS. 12A-12C are perspective schematic views in partial cutaway representing successive positioning of an embodiment of a cover structure disposed in closing relation to the interior of the left atrial appendage.

FIG. 17 is a perspective view in schematic form of the embodiment of FIGS. 15 and 16, wherein the closure assembly is located within the lumen of an introductory instrument and wherein the closure members thereof are in a retracted orientation.

FIG. 18 is a perspective view in schematic form of the embodiments of FIGS. 15 through 17 wherein a first closure member is disposed in an expanded orientation and in at least partially closing relation to a tissue opening to be closed.

FIG. 19 is a perspective view of the embodiments of FIGS. 15 through 18 in schematic form, wherein at least a first closure member of the closure assembly includes a flexible material cover mounted thereon in closing and or at least partially sealing relation to a tissue opening to be closed.

FIG. 20 is a perspective view in schematic form and section representing the closure assembly of the embodiments of FIGS. 1-19 in a closing relation to a tissue opening and in sandwiching relation to tissue in which the tissue opening is formed.

Like reference numerals refer to like parts throughout the several views of the drawings.

DETAILED DESCRIPTION OF THE PREFERRED EMBODIMENT

As represented in the accompanying Figures, the present invention is directed to an introduction assembly and attendant method for the insertion of medical instruments, such as catheters, through a thoracic passage and corresponding intercostal spaces into either a right or left atrium of the heart for the purpose of performing predetermined cardiac maneuvers on intracardiac structures, as required.

Figure 1:
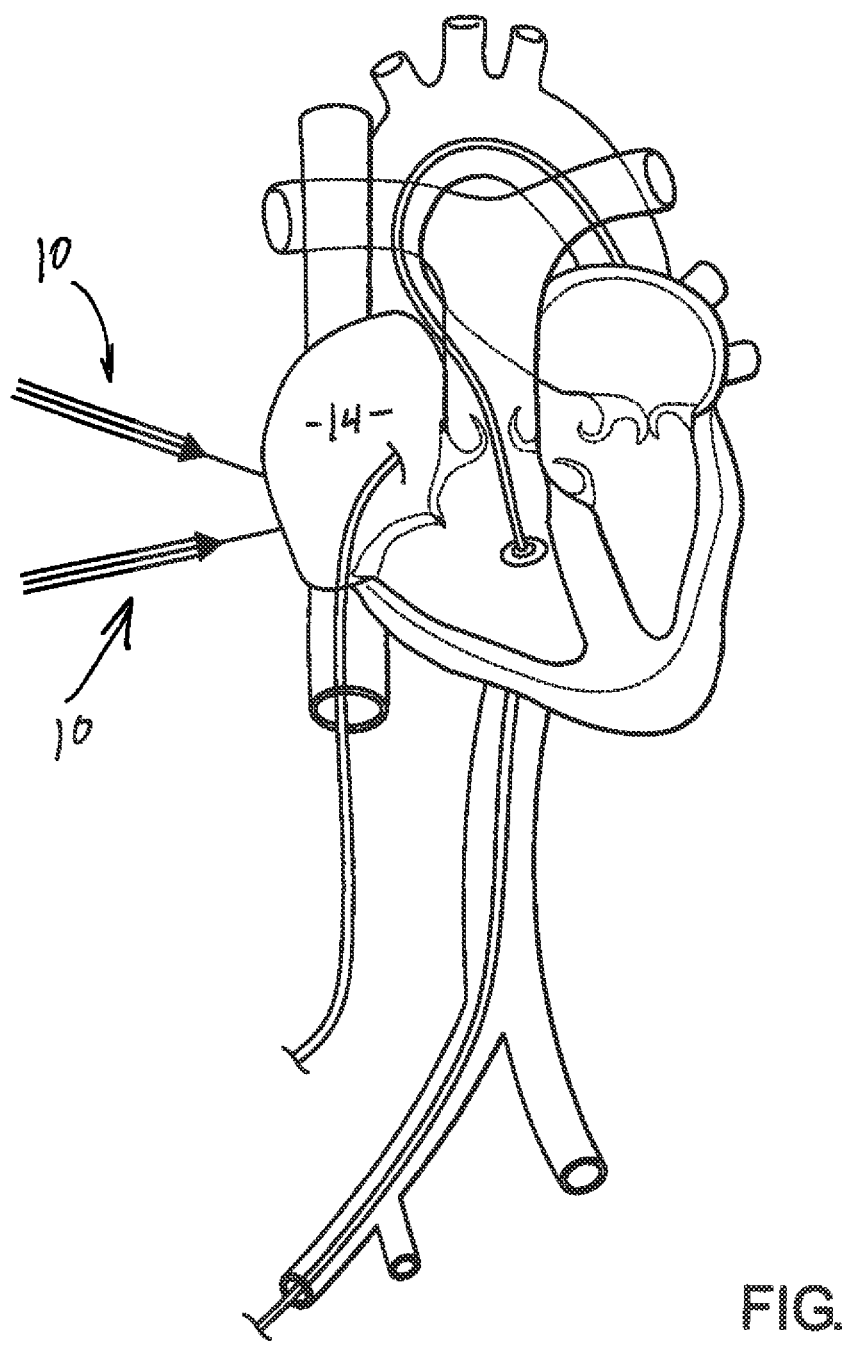
FIG. 1 is a schematic representation of the heart including the implementation of the present invention including the introduction of a plurality of medical instruments into a selected one of the right or left atrium of the heart.
Figure 2B:
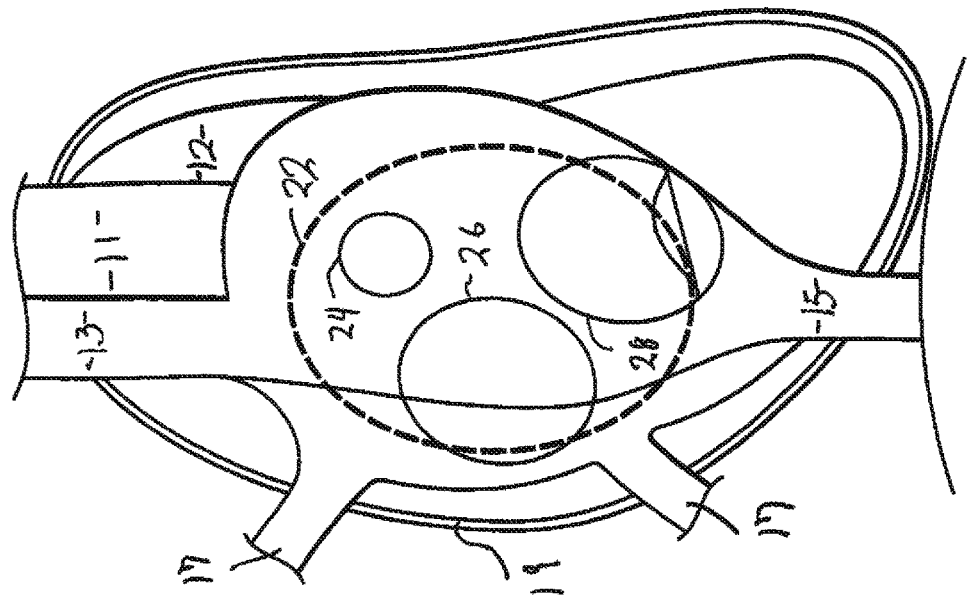
FIG. 2B is a schematic representation of the anatomy of the heart as seen from the right chest and including schematic designations of surgical sites for cardiac maneuvers using the introductory assembly and method of the present invention.
Figure 2A:
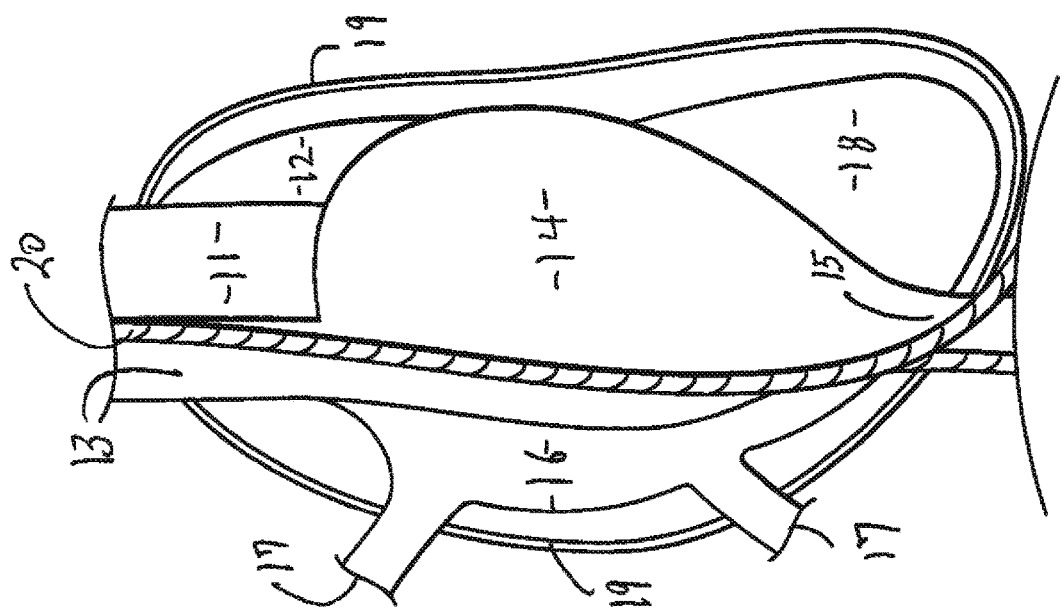
FIG. 2A is a schematic representation of the anatomy of the heart as seen from the right chest.

For purposes of clarity and reference, FIGS. 1, 2A and 2B are schematic representation of the anatomy of the heart. Accordingly, implementing one or more preferred embodiments of the present invention, multiple instruments, including catheters generally indicated as 10, may be concurrently disposed in either the right or left atrium of the heart. As will be set forth in greater detail hereinafter, the instruments 10 pass through the thoracic wall and appropriate ones of intercostal spaces into an interior of a targeted one of the left or right atrium by means of a formed entry site in the pericardium and selected atrium wall. In addition, FIG. 1 presents known or substantially conventional surgical techniques in which catheters are introduced into blood vessels at remote or peripheral sites from the heart and are steered through veins or arteries of the body to reach the heart.

By way of example, the femoral vessels, radial artery, subclavian artery and the jugular veins can be used for the insertion of catheters for remote cardiac intervention. As is well recognized, this peripheral approach avoids many of the risks of open heart surgery but it suffers from significant technical limitations at least partially based on the anatomy and size of the peripheral vessels or a condition existing in some patients resulting in the narrowing or calcification or torturous configuration thereof, making access to the heart difficult, as generally set forth above.

With primary reference to FIGS. 2A and 2B schematic representations of the anatomy of the heart, as seen when viewing the right chest, includes the aorta 11, pulmonary artery 12, superior vena cava 13, right atrium 14 and inferior vena cava 15. Additional representations include the pulmonary veins 17 as well as the right ventricle 18, the pericardial bag 19 and the pulmonary veins 20. For purposes of further reference, FIG. 2B provides a schematic representation of the various surgical sites in which possible cardiac maneuvers may be performed using the assembly and method of the present invention. More, specifically, the perimeter 22 generally defines the zone or area wherein multiple instruments may be concurrently introduced into the right atrium 14 through different thoracic passages and corresponding entry sites by implementing the various preferred embodiments of the present invention. Additional schematic representations include the projection of the left atrial appendage 24; the projection of the mitral valve annulus 26 and the projection of the tricuspid valve annulus 28.

Therefore, required cardiac maneuvering of multiple catheters and other instruments can be individually and cooperatively maneuvered in the indicated surgical sites or zones by implementing the assembly and method, as described in greater detail with reference to FIGS. 3 through 11.

Figure 3:
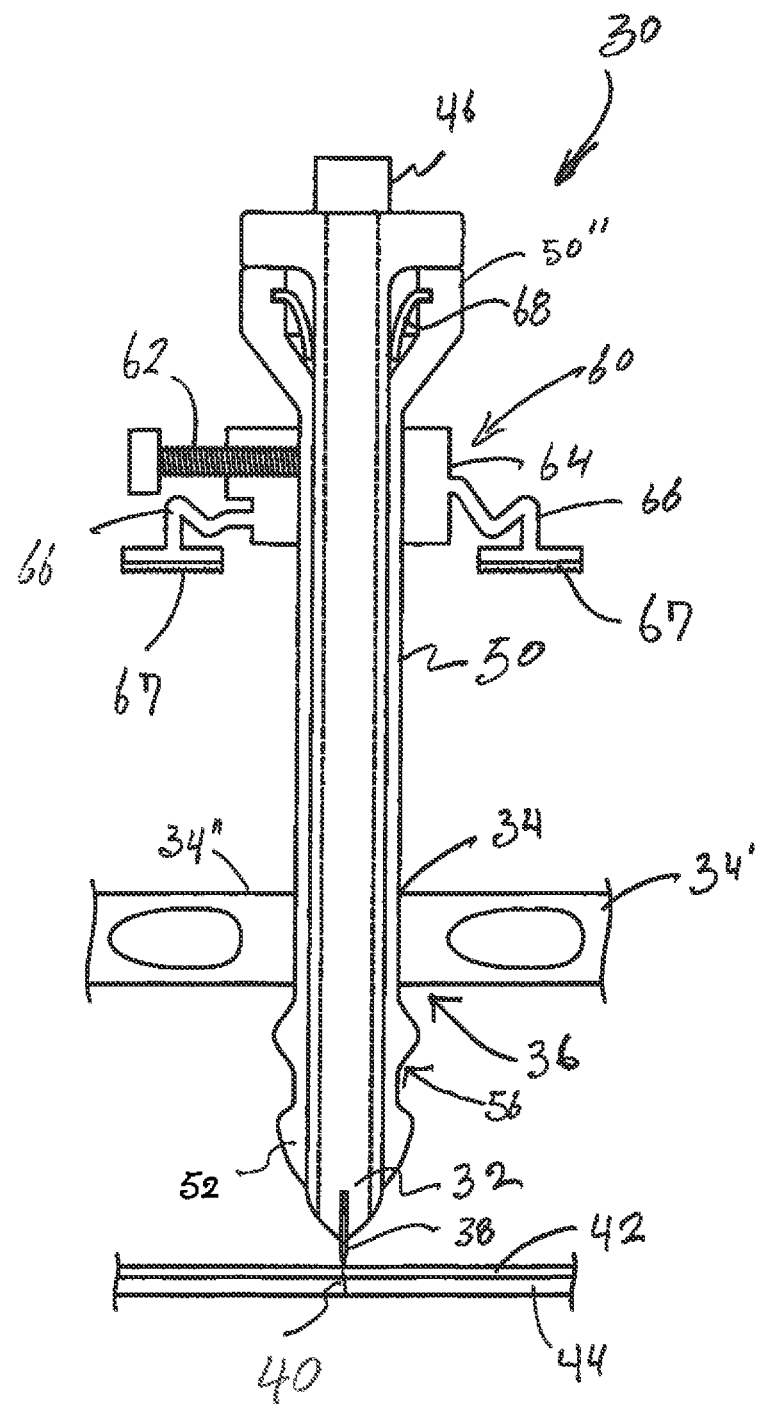
FIG. 3 is a front view in partial cutaway of one preferred embodiment of the introductory assembly of the present invention.
Figure 4:
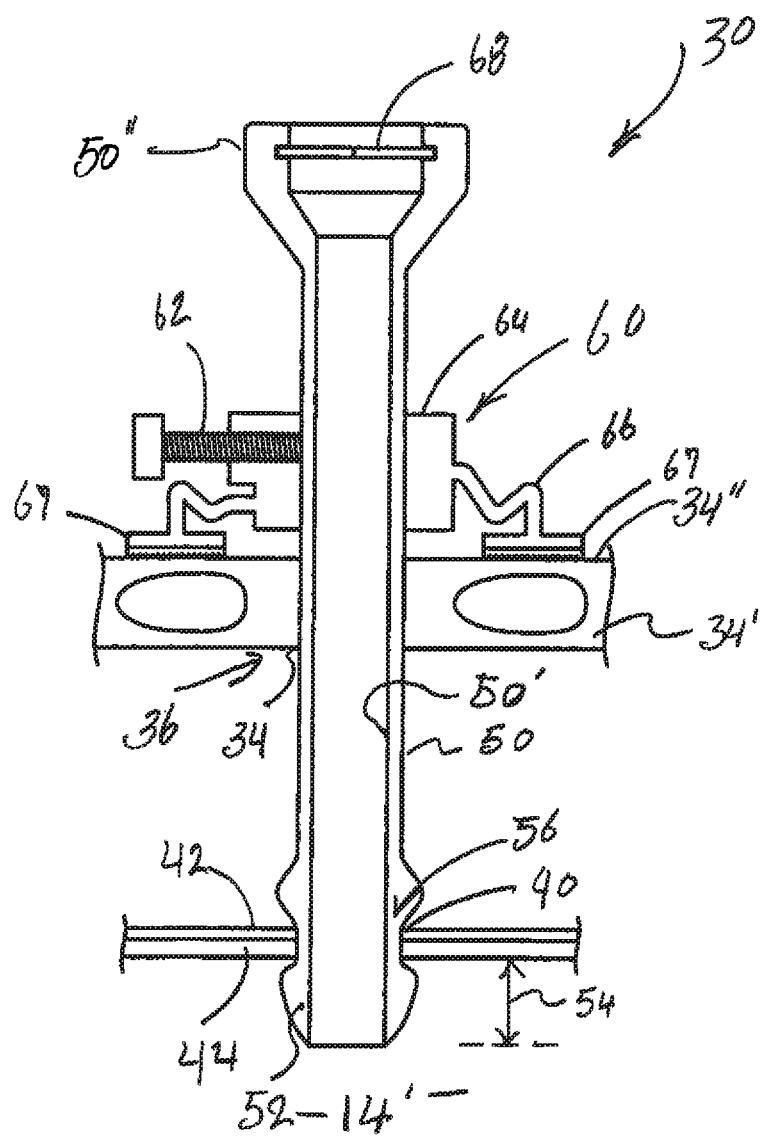
FIG. 4 is a front view of the embodiment of FIG. 3 representing a successive step in the method of implementing the introductory assembly of the present invention.

With initial reference to FIGS. 3 and 4, one preferred embodiment of the introductory assembly is generally indicated as 30. More specifically, a puncturing instrument 32, which may be in the form of a puncturing needle, lancet, etc. is utilized to form a thoracic passage 34 in the thoracic wall 34' through an intercostal space 36 between appropriately positioned ribs, as schematically represented. Further, the lancet 32 may have a puncturing or cutting blade 38 of sufficient structure to form an entry site 40 extending through both the wall 42 of the pericardial bag and the corresponding disposed part of the wall 44 of the selected or targeted atrium 14.

While the puncturing instrument or lancet 32 may vary in construction and operation, one embodiment thereof includes the cutting blade 38 selectively disposable between an outwardly extended, operative position, as represented in FIG. 3, or an inwardly disposed retracted position, not shown for purposes or clarity. In order to accomplish this selective positioning of the blade 38, an accessible positioning member or like structure 46 is connected to the blade 38 and may be mounted on the lancet 32 at generally a proximate end thereof. As such, the positioning member 46 is disposed exteriorly of the thoracic wall 34' and is thereby readily accessible for manipulation by medical personnel to accomplish the extension or retraction of the blade 38, as required. With further reference to FIGS. 3 and 4, an introductory sheath 50 includes a central channel or lumen 50' facilitating the coaxial alignment and overlying, covering relation of the sheath 50 relative to the puncturing instrument 32. Once the entry site 40 is formed, the distal end 52 of the introductory sheath 50 passes there through. As a result, the central lumen 50' of the introductory sheath 50 is disposed in accessible communication with the interior 14' of the selected atrium 14, as generally indicated in FIG. 4.

The passage and positioning of the distal end 52 of the sheath 50 is controlled and/or restricted through the provision of a buffer, generally indicated as 56. As will be apparent from additional description provided hereinafter, the buffer 56 may be defined by a variety of different structures. However, in each of the possible structural modifications, the buffer 56 is disposed and configured to limit or restrict, and therefore at least partially define or determine, the length of the distal end 52 which passes into the interior 14' of the selected or targeted atrium. More specifically, the disposition and structural features of the buffer 56 will determine an "intracardiac length" 54 of distal end 52 which defines the length of the distal end 52 allowed to be inserted within the interior 14' of the selected atrium. While the intracardiac length 54 may vary, the conventional length would be generally from about 1.5 cm to 2 cm. The intracardiac length 54 is sufficient to facilitate entry of intended instruments into the atrium but is at least partially restricted to facilitate manipulation and maneuvering of a catheter or other instrument passing through the introductory sheath 50 into the interior 14' of the targeted atrium. As a result, required cardiac manipulation of intracardiac structure intended for treatment, repair, replacement, etc. may be more efficiently accomplished.

Figure 4A:
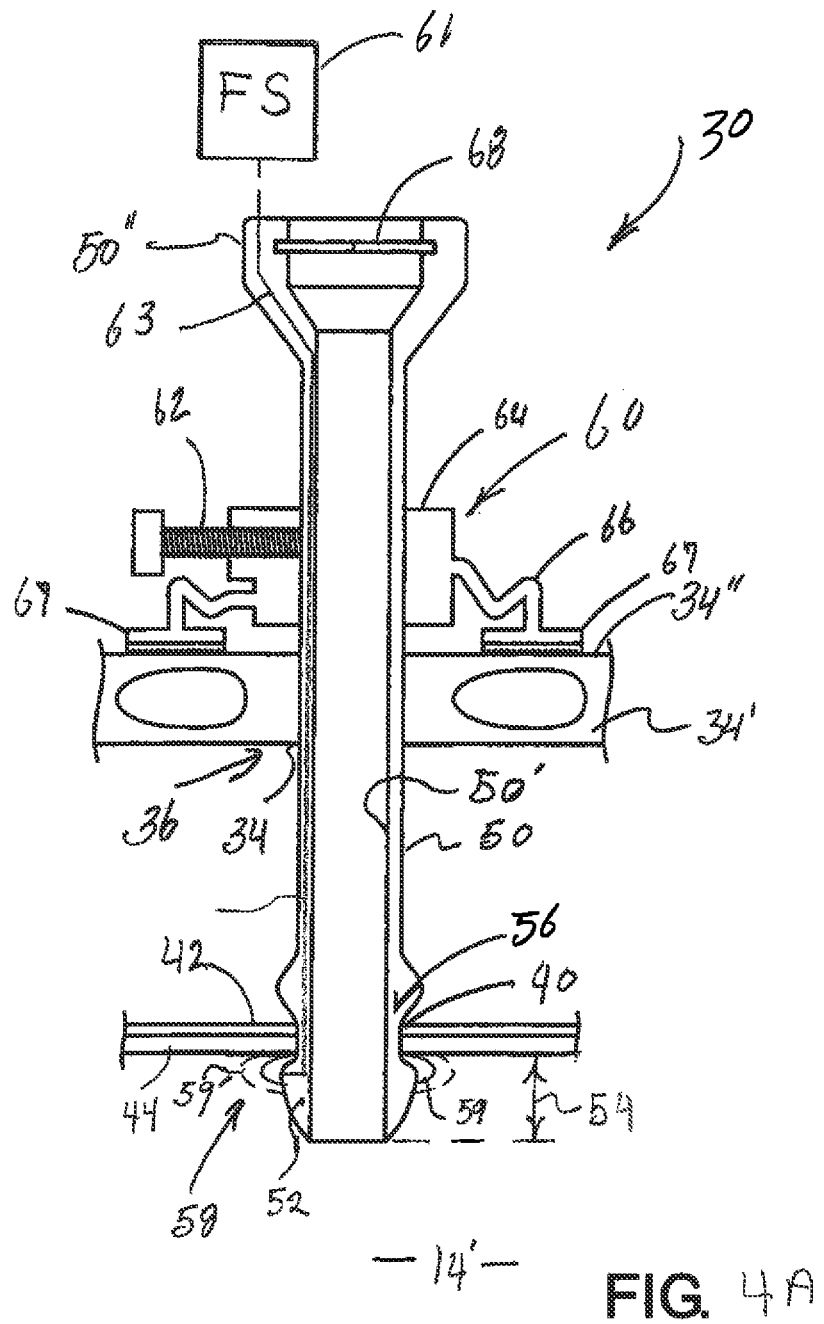
FIG. 4A is yet another preferred embodiment of the present invention structured to be used with the introductory assembly as represented in the embodiment of FIG. 4.
Figure 5:
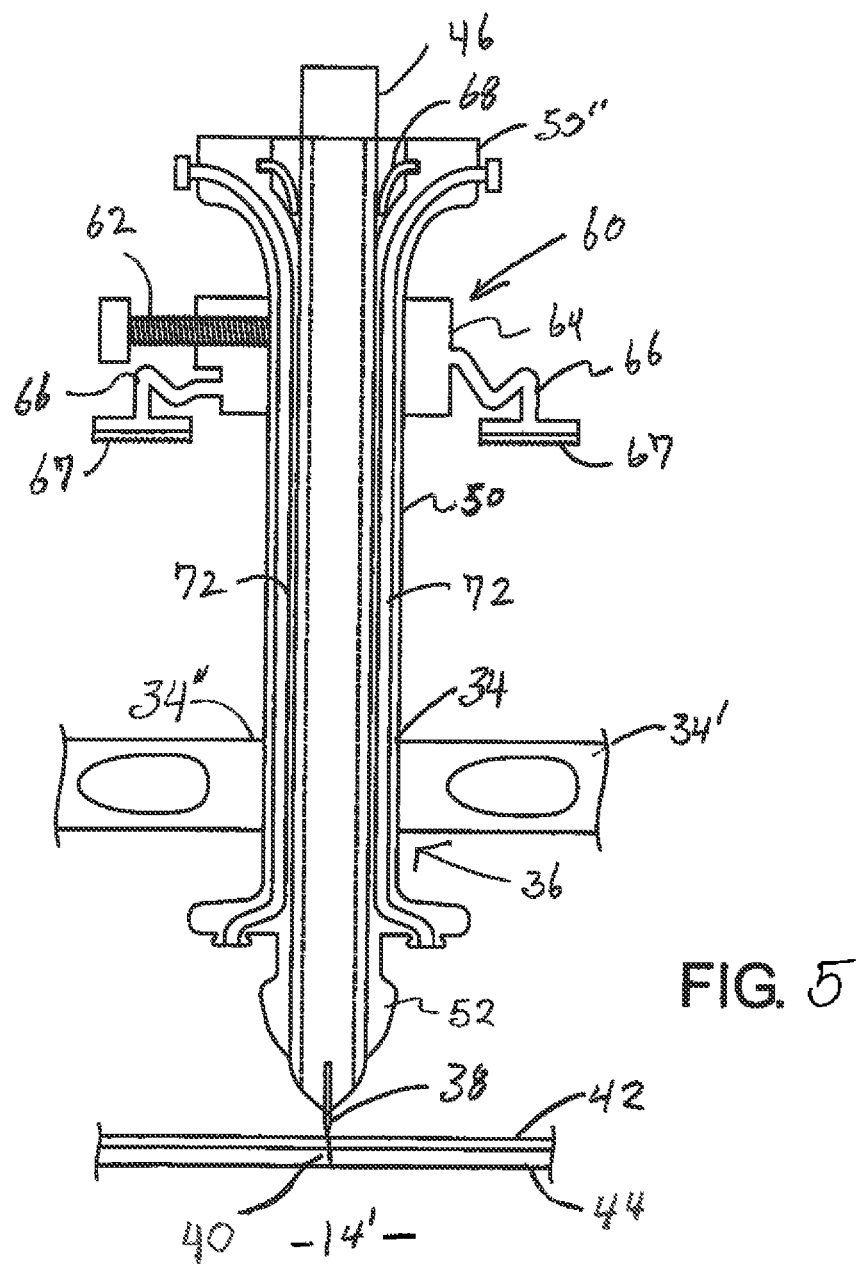
FIG. 5 is another preferred embodiment of the introductory assembly of the present invention similar to but distinguishable from the embodiment of FIGS. 3 and 4.
Figure 6:
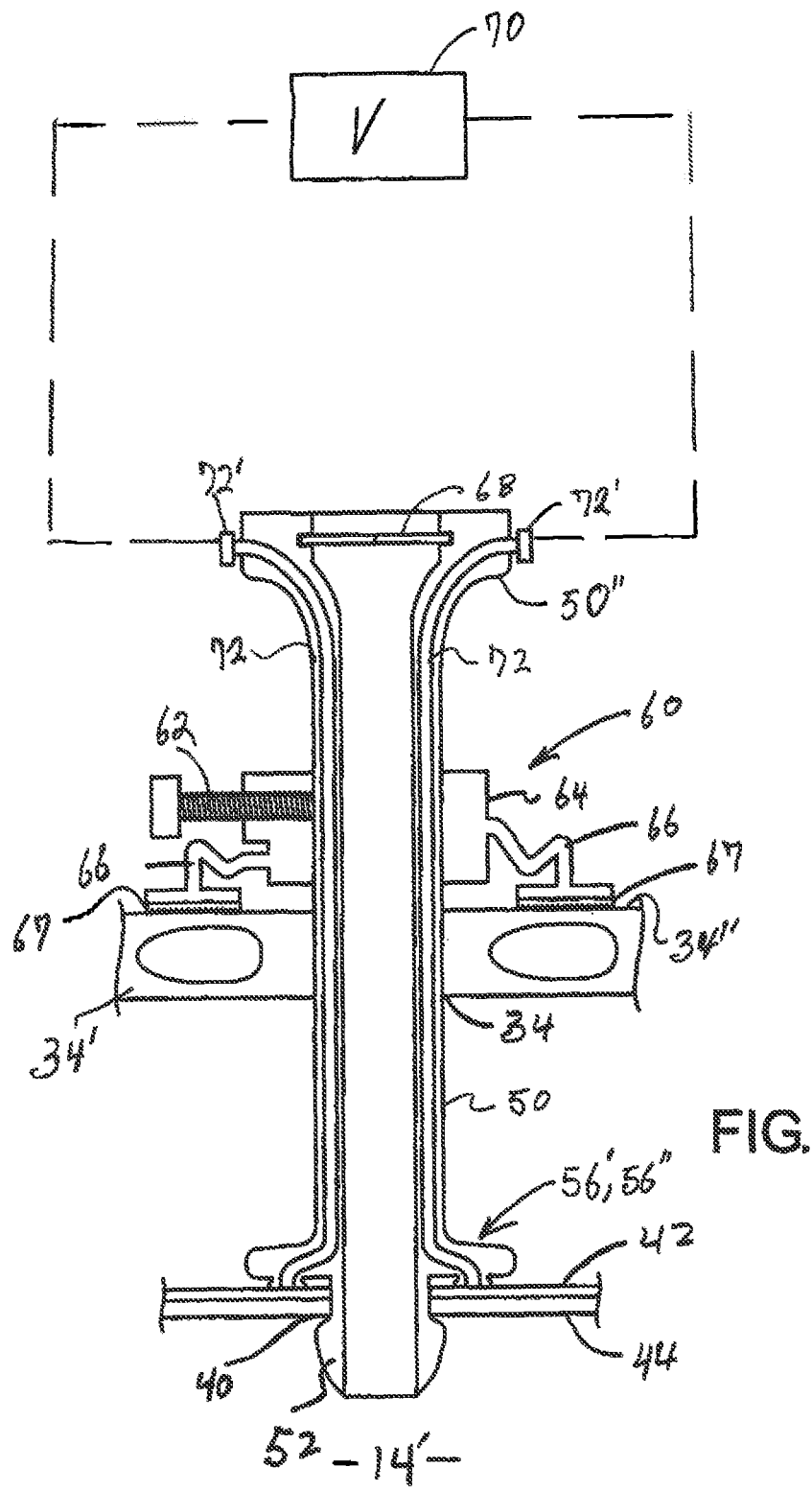
FIG. 6 is a front view of the embodiment of FIG. 5 in a successive step of the method of implementing the introductory assembly of the present invention.
Figure 6A:
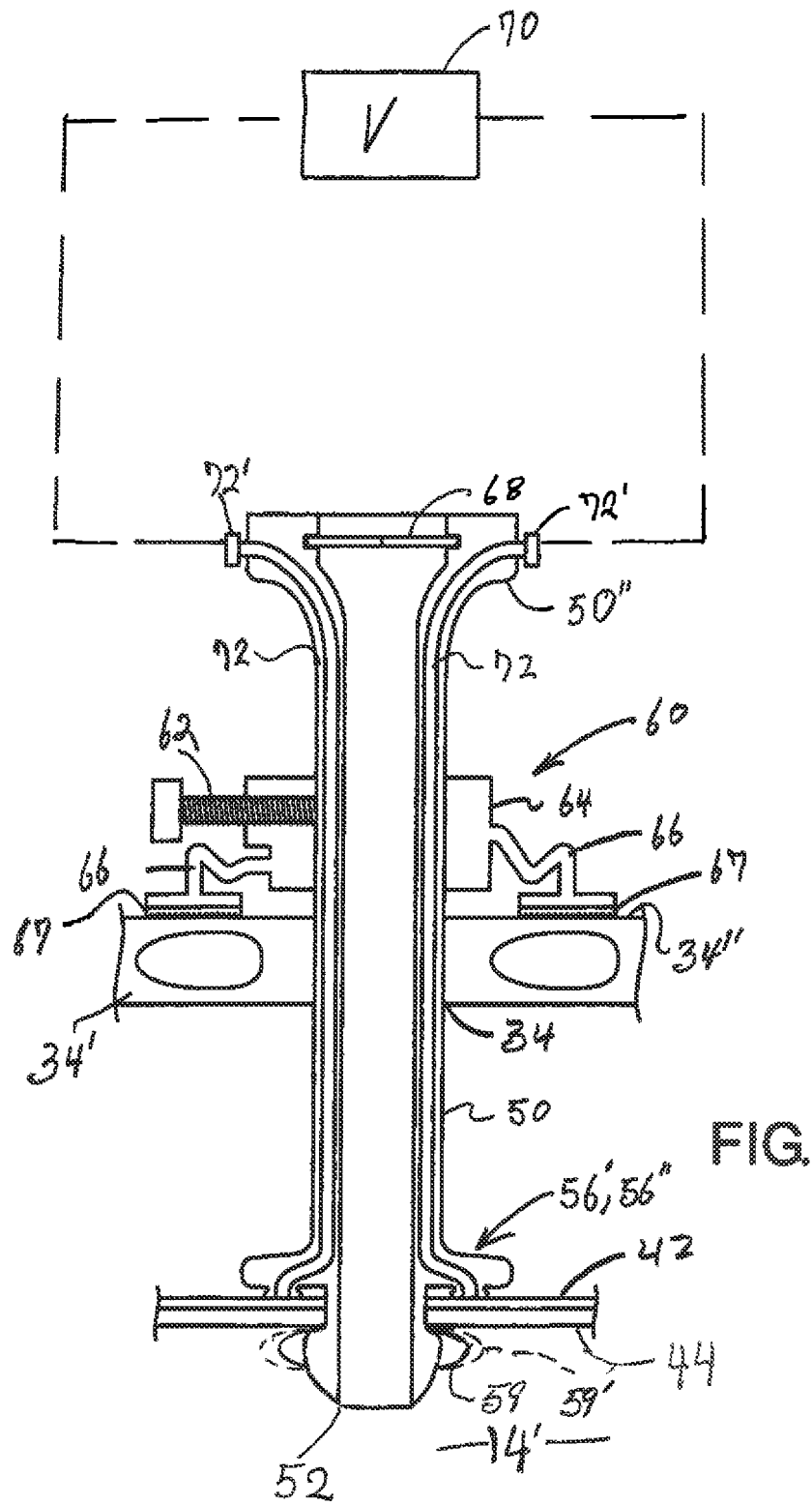
FIG. 6A is yet another preferred embodiment of the present invention structurally and operatively similar to the embodiment of FIG. 4A but modified for use in combination with at least the embodiment of FIG. 6.

Yet another embodiment of the present invention is represented in FIGS. 4A and 6A. More specifically, the present invention further comprises a restricting assembly generally indicated as 58 which is attached to the distal end 52 of the sheet 50. Moreover, the restricting assembly 58 is preferably in the form of an expandable or inflatable bladder 59 connected to the distal end 52 as represented. Further, being expandable or inflatable, the bladder 59 is capable of being selectively disposed into a collapsed position as schematically represented in solid lines in FIGS. 4A and 6A. However, the bladder 59 is also selectively inflated or expanded as at 59' schematically represented in phantom lines in FIGS. 4A and 6A. Accordingly, while in the collapsed position the restricting assembly or bladder 59 assumes a dimension and/or configuration which facilitates its passage through the entry site 40 as it moves with the distal end and passes through the entry site 40 into or out of the interior of the targeted atrium as at 14'. Once within the interior of the targeted atrium, the expandable or inflatable bladder may be activated to assume its restricting orientation 59'. Such an expansion or inflation may be accomplished by the provision of a pressurized fluid source 61 connected in fluid communication, as at 63, of FIG. 4A with the restricting assembly 58 and bladder 59.

Accordingly, once in the restricting orientation 59' the bladder 59 assumes a dimension and/or configuration, extending outwardly from the distal end 52 sufficient to prevent or significantly restrict the removal of the distal end 52 from the interior of the targeted atrium. Accordingly, the restriction assembly 58 may be used in combination with or independent of the buffer 56, as represented in FIG. 4A or the additional embodiment 56' and 56" of the buffer as represented in FIG. 6A. It should be apparent that the restricting assembly 58 may also facilitate maintenance of the intracardiac spacing 54 of the distal end 52 when disposed within the interior of the targeted atrium 14 as represented in both FIGS. 4A and 6A. For purposes of clarity, the pressurized fluid source 61 and the fluid communicating connection 63 is absent from the representation of FIG. 6A.

Additional structural and operative features of the introductory assembly 30 include a stabilizing assembly 60 adjustably and/or movably connected to the introductory sheath 50. The stabilizing assembly 60 is selectively positioned relative to the exterior of sheath 50 into and or out of engagement with the exterior surface 34" of the thoracic wall 34'. Moreover, the structural and operative features of the stabilizing assembly are such as to maintain a preferred and/or predetermined angular orientation of the sheath 50 relative to the thoracic wall 34' as the sheath 50 passes through the thoracic passage 34 and the entry site 40. While the schematic representations of FIGS. 4-6 and 9-11 show a substantially perpendicular or direct inline relation between the axis of the sheath 50 and the thoracic wall 34', FIG. 1 more accurately indicates that the various instruments 10 may assume a variety of different angles as they extend through the thoracic wall into the selected atrium. Therefore, the stabilizing assembly 60 includes a lock or like fixing member 62 movable relative to a base 64 into a removable locking engagement with the exterior of the introductory sheath 50. In addition, adjustable legs or like members 66 have engaging pads 67 structured to resist or restrict relative movement between the exterior of the pad 67 and the exterior surface 34" or the thoracic wall 34' to which the stabilizing assembly 60 is removably secured. As a result, the stabilizing assembly 60 facilitates the maintenance of the sheath 50 and instruments passing there through at a preferred predetermined angular orientation relative to the thoracic wall 34'.

As also indicated in one or more of the various preferred embodiments of introductory sheath 50, a valve structure generally indicated as 68 is connected at or adjacent to the proximal end 50". More specifically, the valve structure 68 is disposed within a portion of the interior lumen 50' and is structured to facilitate the passage of instruments into and through the lumen 50' as they are introduced into the open proximal end 50", as clearly represented in FIGS. 5 and 9 through 11. However, the valve structure 68 will automatically close absent the existence of instrumentation within the interior lumen. In its closed orientation, as represented in FIGS. 4 and 6, the valve structure is operatively disposed to prevent back bleeding and/or air embolism and while enabling the sequential introduction of dedicated catheters to perform the intracardiac maneuvers.

Therefore, the valve structure 68 may be considered, but is not limited to, a one way valve structure which may include an inherent bias or other operative structure which facilitates its closure into fluid sealing relation to the interior lumen 50' absent the presence of instrumentation within the lumen 50'.

As represented in FIGS. 5 through 11 yet another preferred embodiment of the present invention comprises structural modifications of the buffers, generally indicated as 56' and 56". The structural and operative differences are described in greater detail with primary regard to FIGS. 7A, 7B, and 8A, 8B. More specifically, each of the buffers 56' and 56" is secured to the exterior of the pericardial bag 42 by means of vacuum or negative pressure generated by a vacuum source generally indicated as 70. The vacuum source 70 is connected in fluid communication to the buffers 56', 56" by means of appropriate conduits 72 or other interconnecting flow communicating structure. As such, the flow communicating structures or conduits 72 may be mounted on or at partially within the introductory sheath 50.

As selectively operated, the vacuum source 70 may produce a negative pressure on or with the buffer structure 56', 56" which in turn is exerted on the exterior surface of the pericardial bag 42. As a result, the buffers 56' and 56" will be maintained in a secure, stable but removable engagement with the exterior of the pericardial bag 42. Such a removable securement will further facilitate the stable, intended positioning of the distal end 52 within the interior 14' of the targeted atrium.

Figure 10:
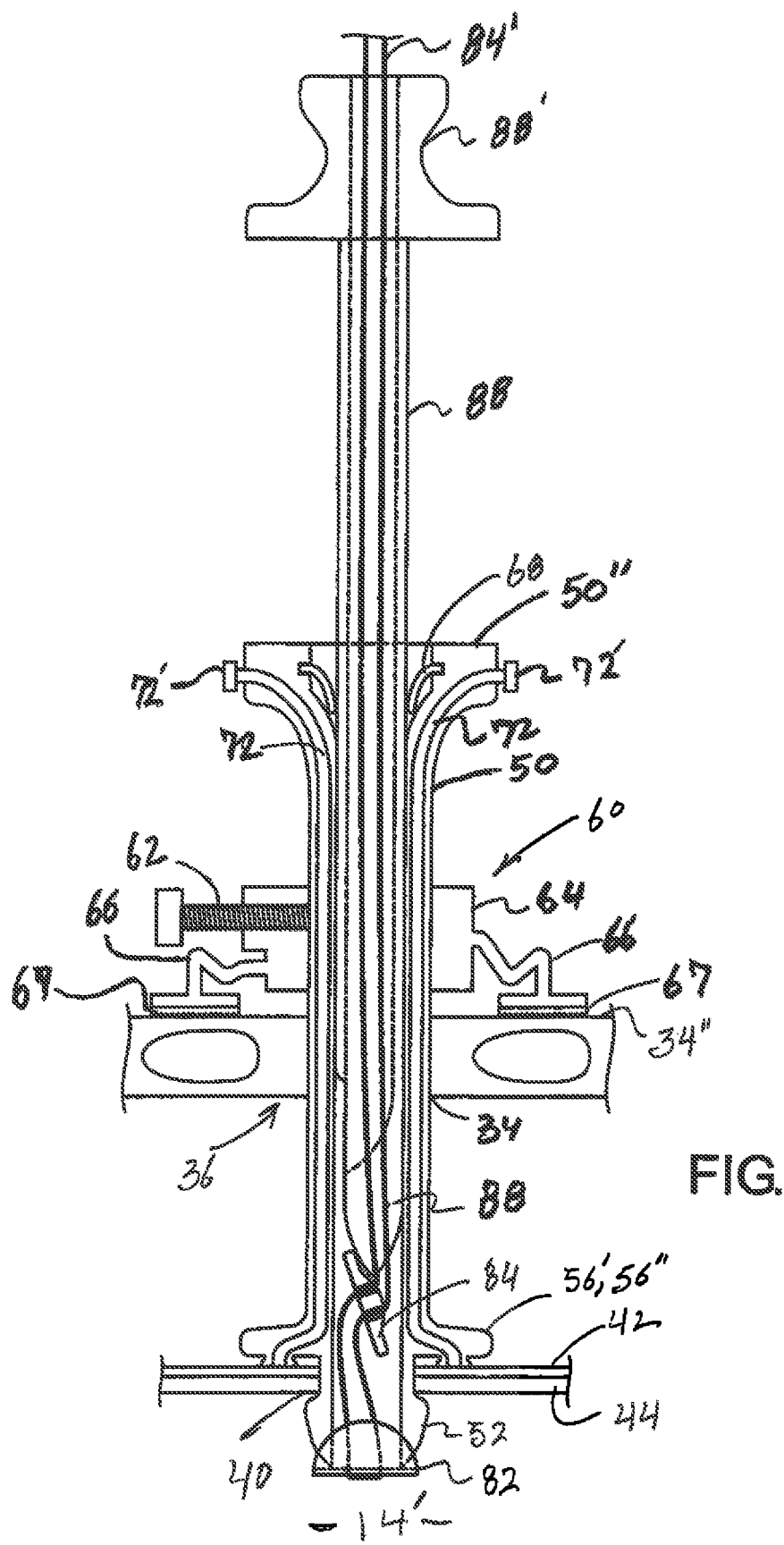
FIG. 10 is a front view of the representing the method of implementing the introductory assembly of the embodiment of FIG. 9.
Figure 11:
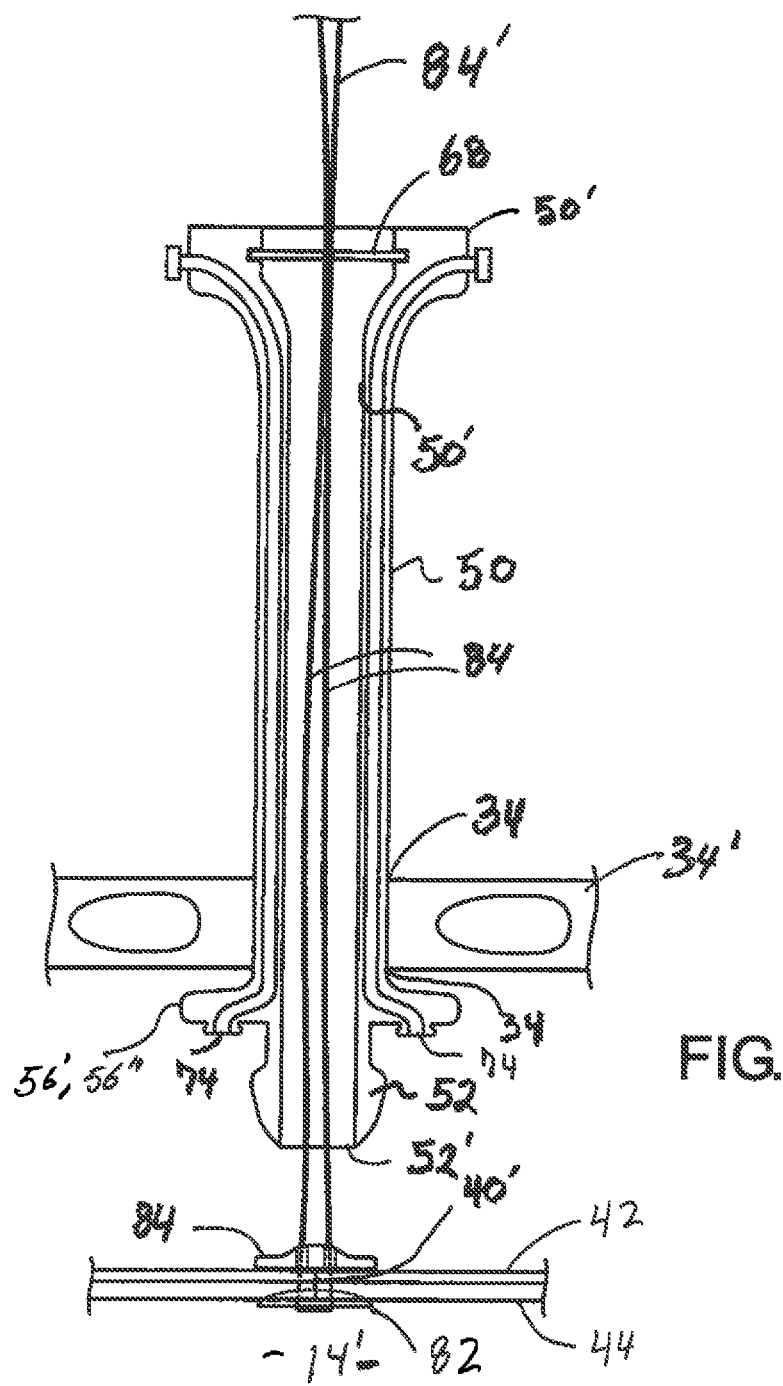
FIG. 11 is a front view representing an additional step of the method of implementing the introductory assembly of the embodiment of FIGS. 9 and 10.

As should be apparent, control or regulation of the negative pressure exerted by the buffer 56', 56" on the pericardium 42 may be regulated by the operation of the vacuum source 70. Therefore, when activated sufficient negative pressure is exerted on the exterior surface of the pericardium 42 by the buffer 56', 56" in order to maintain the buffer 56', 56" in secure engagement therewith. However, by diminishing or eliminating the negative pressure, by regulating the operation of the vacuum source 70, a detachment of the buffer 56', 56" as well as the introductory sheath 50 from the entry site 40, as represented in FIG. 11, can be easily accomplished. Additional structural features associated with FIGS. 6 through 11 include the vacuum or negative pressure source 70 being removably connected to the proximal end 50" of the introductory sheath 50 by appropriate connectors 72' attached to or associated with the fluid flow conduits 72.

Figure 9:
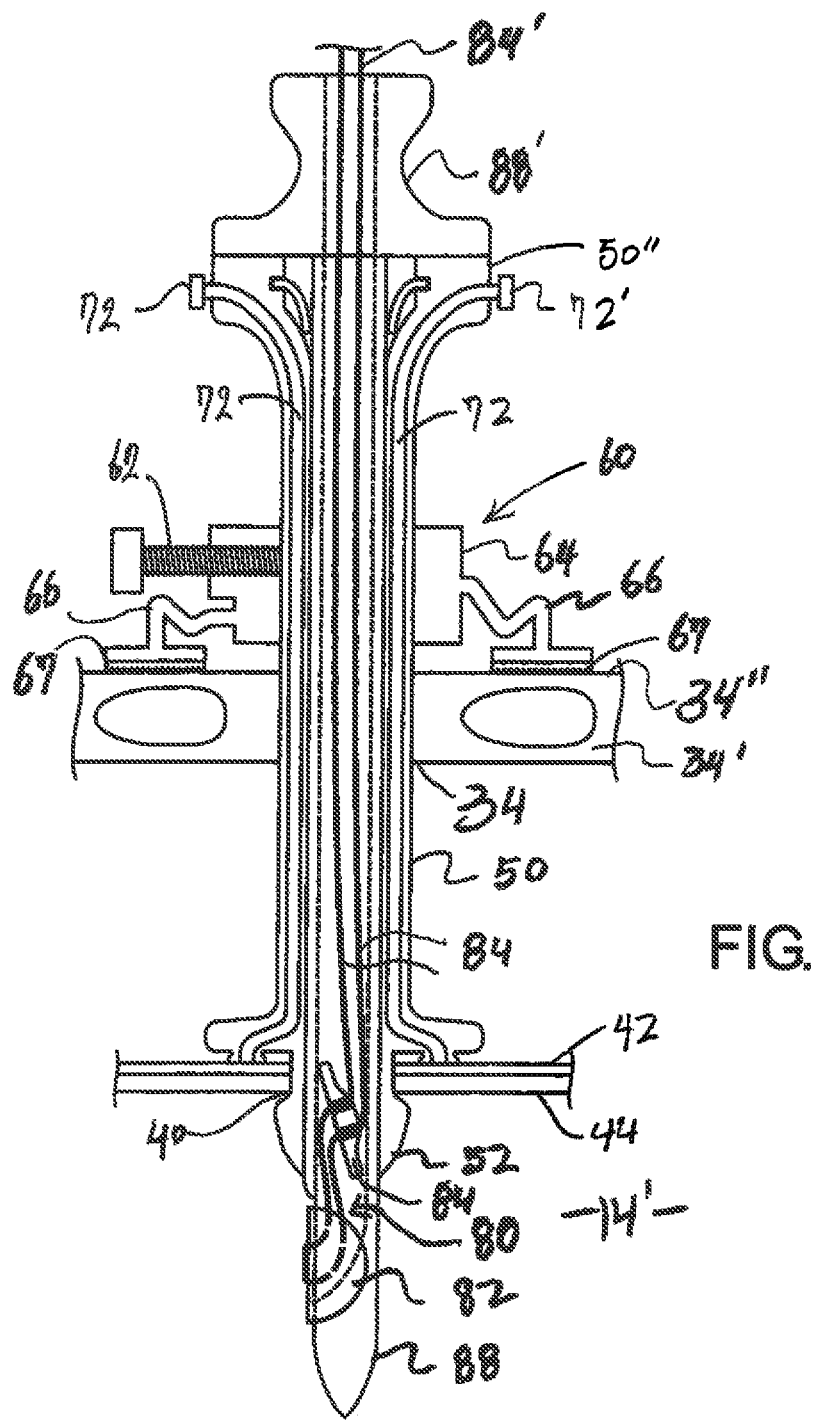
FIG. 9 is front view in partial cutaway of the method of implementing the introductory assembly of the embodiment of FIGS. 5 and 6.

With primary reference to the embodiment of FIGS. 7A and 7B, the buffer 56' comprises a substantially annular configuration including at least one but more practically a plurality of openings 74 formed in the under surface thereof. As should be apparent, the openings 74 are disposed in direct fluid communication with the exterior surface of the corresponding pericardial bag 42 as represented in FIGS. 6 and 9-10 and thereby exert the aforementioned negative pressure on the outside or exterior surface of the pericardial bag 42. As set forth above, the negative pressure is sufficient to maintain a secure engagement of the buffer 56' with the exterior surface of the pericardial bag 42 thereby maintaining the stability and accurate disposition of the introductory sheath 50.

With primary reference to FIGS. 8A and 8B, yet another embodiment of the buffer 56" is represented which includes at least one but preferably a plurality of outwardly extending pads 57. Each of the pads 57 is disposed in fluid communication with the vacuum source 70 through the aforementioned conduits or like flow communicating structures 72. Somewhat similar to the embodiment of FIGS. 7A and 7B, the pads 57, defining the buffer 56", also include a plurality of opening 74 which are disposed in confronting engagement of the exterior surface of the pericardium 42 and thereby exert a suction or negative pressure thereon. The exerted negative pressure is sufficient to maintain the buffer 56" into a stable but removable connection with the pericardial bag 42 substantially adjacent the entry site 40. Additional structural features of the buffer 56" include its ability to be selectively disposed in a collapsed or retracted orientation as represented in phantom lines in FIG. 8A. As should be apparent, when in the collapsed position, the pads 57 of the buffer 56" take up less room thereby facilitating the positioning thereof into the intended operative position as they are disposed through the thoracic passage 34 of the thoracic wall 34'.

Further, the positioning or orientation of the pads 57 in the operative position may be at least partially "automatic" by structuring the pads from a material which has at least a minimal inherent bias. Once the buffer 56" is disposed in confronting and/or adjacent relation to exterior surface of the pericardium 42 the inherent bias of the material from which the pads 57 are formed will facilitate their "automatic" outward orientation into the operative position of FIGS. 8A and 8B.

Yet another embodiment of the present invention is represented in FIGS. 9 through 11 and is related to a closure assembly generally indicated as 80. However, it is emphasized, that the closure assembly 80, while specifically represented for use with the embodiments of FIGS. 5 through 11 is also operatively structured for use with the embodiments of FIGS. 3 and 4 as described above. Therefore, the closure assembly 80 is selectively disposable within the lumen 50' of the introductory sheath 50 and for positioning in closing or sealing relation to the entry site 40 An operative positioning of the closure assembly 80 is accomplished upon a removal of the distal end 52 from the interior 14' of the selected atrium, as represented in FIG. 11. For purposes of clarity the closed or sealed entry site is represented in FIG. 11 as 40'. Moreover, the closure assembly 80 includes a first segment 82 and a second segment 84 at least initially disposed in separated relation to one another. However, in at least one preferred embodiment of the closure assembly 80 includes an interconnecting structure, such as a cord or like structure 84, which may be manipulated interconnect the first and second segments 82 and 84 into the closing relation to the entry site 40'. As such, the interconnecting structure 84 extends through substantially the entire length of the lumen 50' and includes a portion 84' which is assessable from the exterior of the introductory sheath 50, as clearly indicated. As implemented, the first segment 82 passes into the interior 14' of the selected atrium through the open entry site 40 formed in the pericardium 42 and the atrium wall 44. Such interior positioning of the first segment 82 may be accomplished by appropriate instrumentation 88 which also may be in the form of a positioning catheter or like structure. The instrumentation 88 also passes through the interior lumen 50' of the introductory sheath 50 and includes a positioning member 88' protruding outwardly from the open proximal end 50" of the introductory sheath 50 as represented in FIGS. 9 through 11. With primary reference to FIG. 10, once the first segment is disposed on the interior 14' of the selected atrium, the second segment 84 is disposed or remains within the interior lumen 50' adjacent to the distal end 52. Once the first segment 82 is disposed on the interior 14' of the atrium, the distal end 52 of the introductory sheath 50 is removed from the interior 14' of the selected atrium and passes back through the open entry site 40 along with the second segment 84 remaining on the interior of the lumen 50'.

Subsequent to the removal of the distal end 52 of the introductory sheath 50 from the entry site 40 and upon closure of the entry site 40, as at 40', the positioning instrument 88 will serve to remove the second segment 84 from the interior lumen 50' through the opening 52' of the distal end 52. Appropriate manipulation of the exterior, accessible end 84' of the interconnecting structure 84 will then serve to dispose both the first segment 82 and the second segment 84 into the closing relation to the now closed entry site 40' as clearly represented in FIG. 11. When in the operative closing relation as represented in FIG. 11, the first closing segment 82 will be disposed in confronting engagement with the interior surface of the selected or targeted atrium wall 44. In cooperation therewith, the second exterior closing segment 84 will be disposed in confronting engagement with the exterior surface of the pericardium 42. As such the closed entry site 40' will thereby be effectively "sandwiched" therebetween to prevent leakage or passage of fluid therethrough. This closing sealing relation of the closing assembly 84, relative to the closed entry site 40', will facilitate the healing thereof.

Additional features of the closure assembly 80 and specifically including the first and second closing segments 82 and 84 are their formation from a material which has an at least minimal inherent bias. As such, both the first and second closing segments 82 and 84 may be disposed in at least partially folded or otherwise collapsed orientation as they pass through the interior lumen 50' of the introductory sheath 50. However, once passing out of the opening 52' of the distal end 52, the "inherent bias" of the material of the first and second closing segments 82 and 84 will facilitate their "automatic" expansion into the operative position clearly represented in FIG. 11. Also of note is the forming of the first and second closing segments 82 and 84 from a material that will eventually dissolve on a timely basis by the exposure to ambient bodily fluids. The time in which the first and second closing segments 82 and 84 will be dissolved effectively coincides to the healing of the closed entry site 40'.

Accordingly, the introduction assembly and method for the insertion of medical instrumentation through a thoracic passage into a targeted atrium of the heart overcomes many of the disadvantages and complications associated with conventional or known related surgical procedures, as set forth above.

By implementing one or more of the embodiments of FIGS. 3 through 11, the attendant method comprises forming at least one, but if required, a plurality of entry sites 40 into a targeted atrium 14 and positioning different introductory sheaths 50 through different thoracic passages 34 and corresponding ones of the formed entry sites 40. The distal end 52 of each of the introductory sheaths 50 is inserted through corresponding entry sites 40 into the interior 14' of the selected atrium 14 to a depth corresponding to the intracardiac length 54 of the inserted distal end 52. Once the one or more sheaths 50 are inserted through respective ones of the entry sites 40, catheters or other instruments dedicated to perform predetermined cardiac maneuvers pass through the one or more introductory sheaths 50 into the targeted atrium 14 through the corresponding entry sites 40. Thereafter and upon completion of the required cardiac maneuvers, the inserted catheters or instruments are removed from the interior 14' of the targeted atrium 14 back through the central lumen 50' of the respective introductory sheaths 50.

In order to close or seal the entry sites 40 a plurality of closure assemblies 80 are passed through the interior lumen 50' of each of the one or more introductory sheaths 50. In establishing a closing relation of the closing assemblies 80 with the entry sites 40, a first closing segment 82 and a second closure segment 84 of each closure assembly 80 are respectively disposed interiorly and exteriorly of the entry site 40. As such, the entry sites 40, or 40' when closed, are disposed in a substantially "sandwiched" relation between the corresponding first and second closure segments 82 and 84. After operative positioning of the closure assemblies 80, each of the one or more introductory sheaths 50 are removed from the operating field by movement back through the respective thoracic passages 34.

Yet additional preferred embodiments of the present invention include a portion of said sheath 50 formed of a flexible material. Moreover, the flexible material should be structured to demonstrate sufficient and/or a predetermined minimum amount of flexibility to accommodate relative movement between the pericardial bag 42 and at least the corresponding wall 44 of the targeted atrium 14 adjacent to the entry site 40. In addition, this predetermined amount of flexibility should be sufficient to eliminate or significantly reduce the possibility of tearing, ripping or like damage being done to the relatively fragile wall tissue 44 of the targeted atrium 14. Absent this sufficient flexibility in the distal end 52, as well as a length of the sheath 50 extending from the distal end and engaging, passing through and/or correspondingly disposed with the entry site 40, damage of the targeted atrium wall 44 may occur. Such damage may be the result of, but not limited to, forces placed on the atrium wall 44 and/or pericardium bag 42 by a non-flexible portion of the sheath 50 which passes through or is sufficiently close to the entry site 40 and/or which is disposed within the targeted atrium 14, when relative movement or displacement occurs between the pericardium bag 42 and the atrium wall 44.

Accordingly, the introduction assembly and method of the present invention for the insertion of medical instruments through a thoracic passage into a targeted atrium of the heart are believed to overcome many of the disadvantages and complications associated with conventional or known related surgical procedures, as set forth above.

Figure 12A:
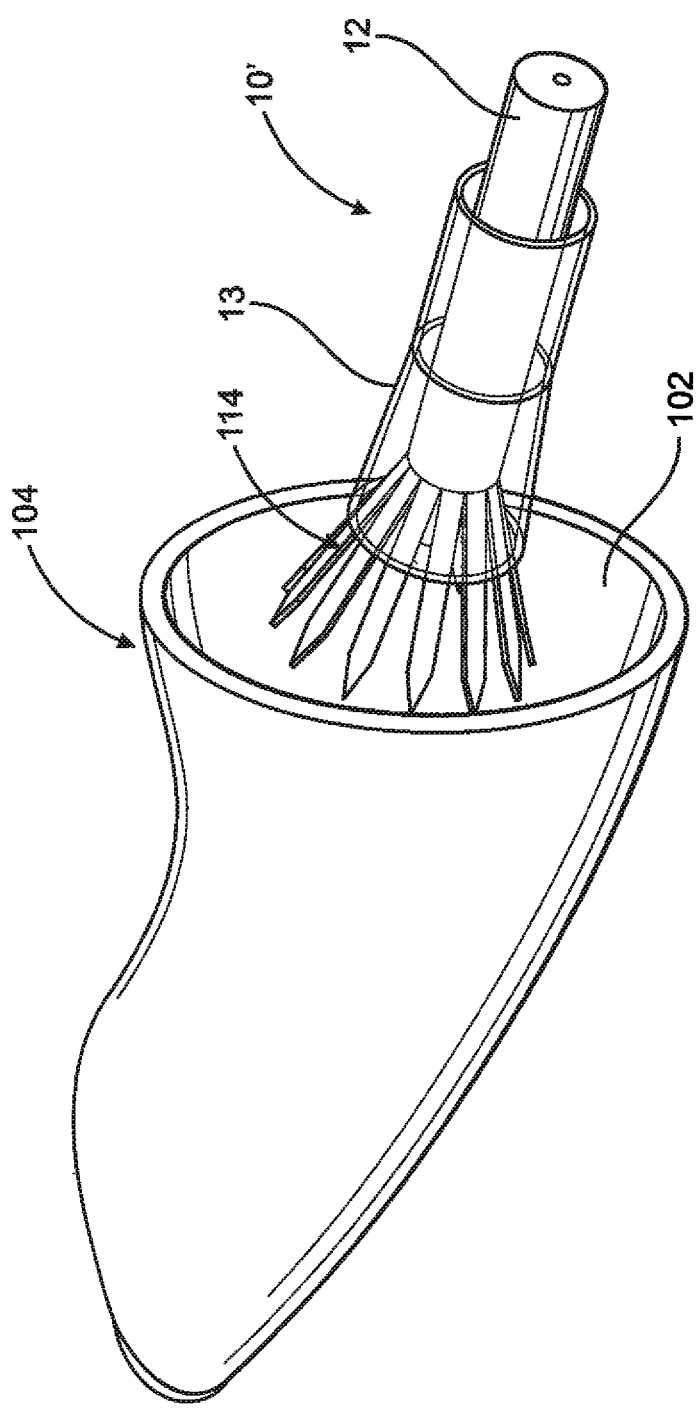
Figure 12B:
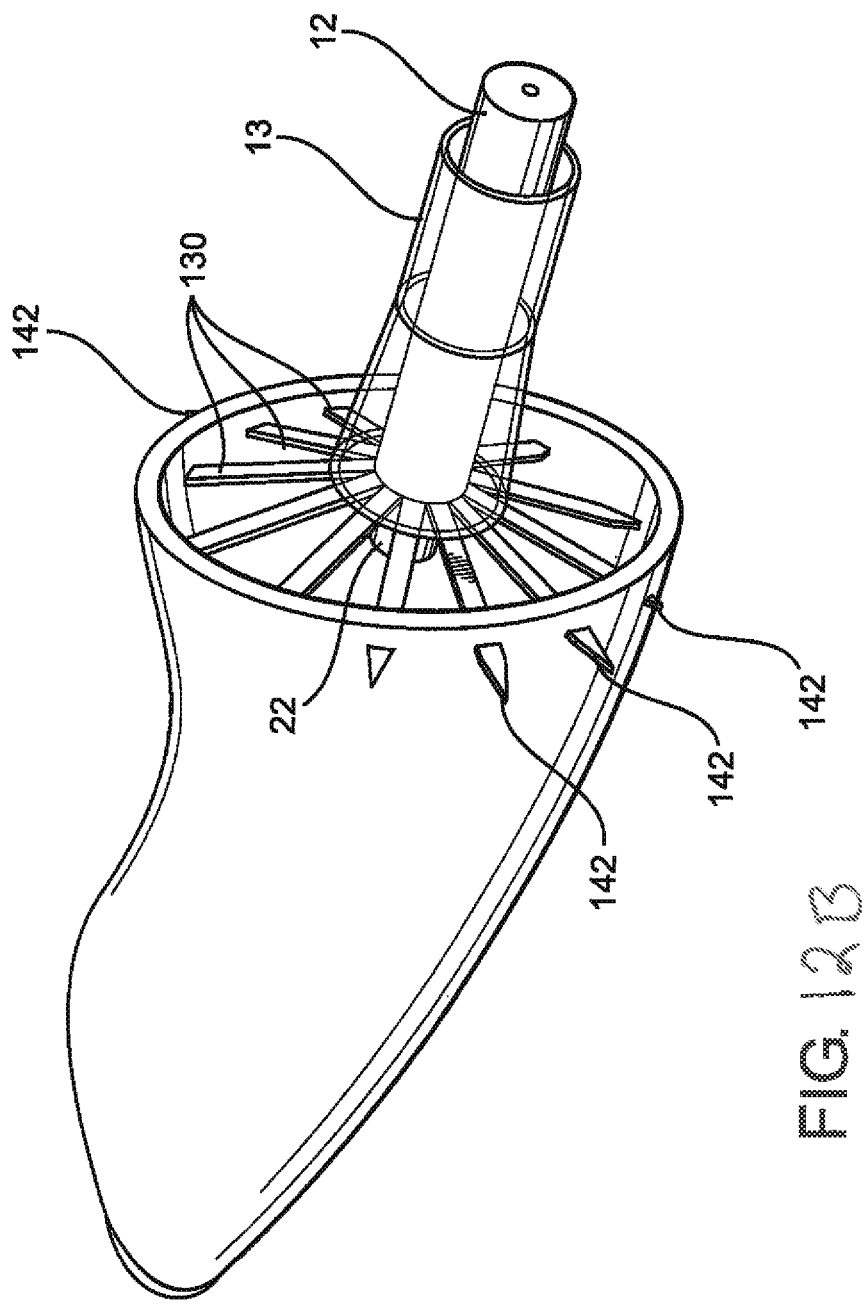

Yet another embodiment of the present invention includes a structural and operative variation of a cover structure primarily, but not exclusively, used to cover the opening of the left atrial appendage is generally represented as 114 in FIG. 12A-12C. More specifically, the cover structure 114 comprises a plurality of ribs 130 structured and initially disposed to move with and relative to an introductory instrument or catheter 112. Moreover, the ribs 130 may be extended out of the open distal end of the catheter 12 and through an outer sheath or like structure 113 into a radially expanded, closing orientation relative to the entrance to the interior 104 of the left atrial appendage 102, as represented in FIGS. 12A and 12B. Although not shown in FIGS. 12A-12C, Dacron or other appropriate material may be used to cover and at least partially define the outer face of the cover structure 114.

Moreover, each or at least some of the ribs 130 include a pointed or other appropriately configured outer end 142 which engages and connects, such as by penetration, to the tissue substantially comprising the outer periphery of the entrance 100 of the left atrial appendage 102. Such positioning of the outer ends 142 will maintain the cover structure 114 in the expanded orientation and closing relation to the entrance opening 100 of the interior 102 as represented in FIGS. 12B and 12C. Once so positioned and after the single strand 20 of occlusion material 106 has been progressively passed into the interior 102 in the form of the arbitrarily intermingled array 110, the remainder of the delivery instrument 110' and catheter 112 are detached from the cover structure 114 and removed from the site.

Figures 13, 14:
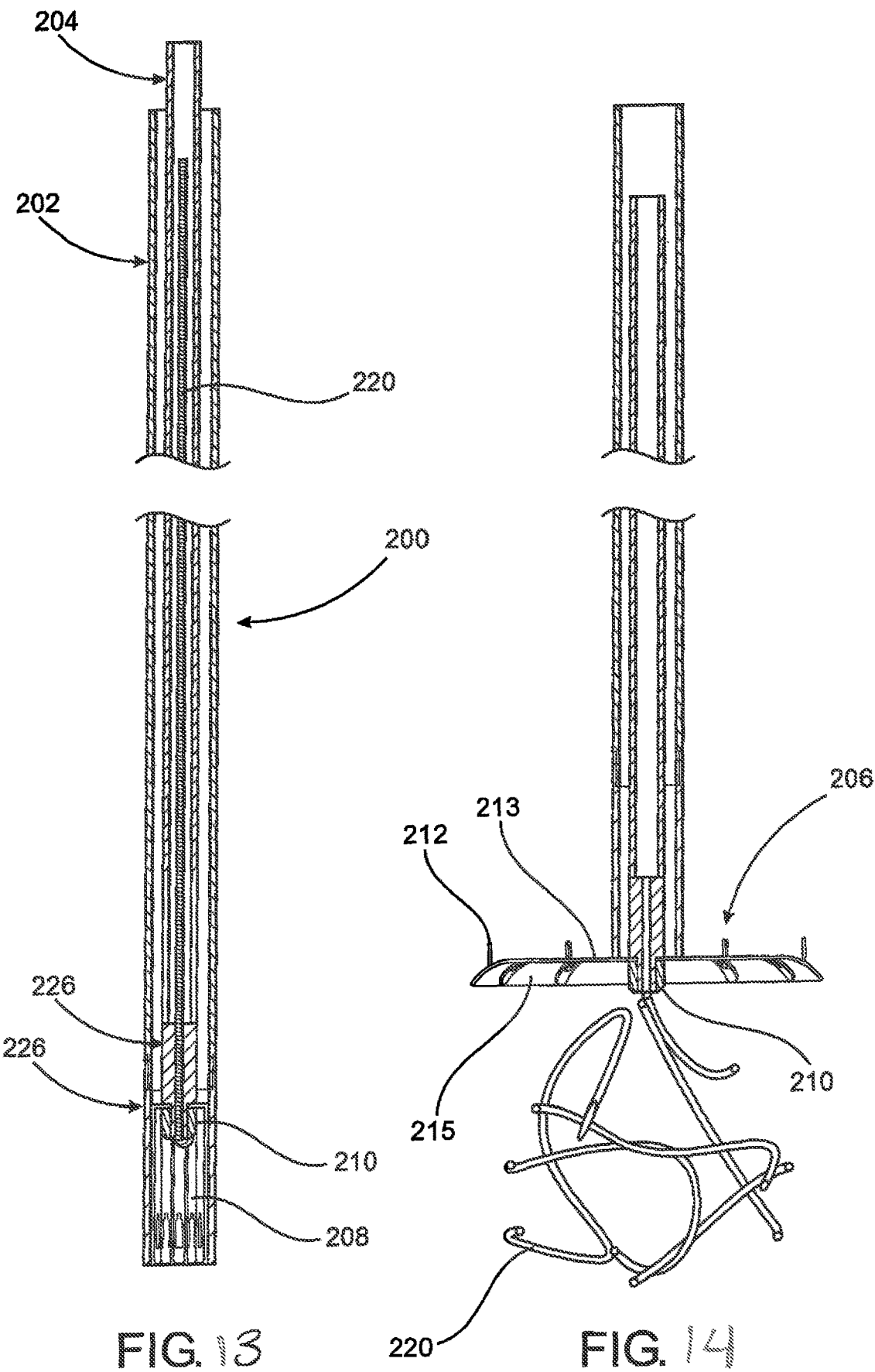
FIG. 13 is a longitudinal sectional view of an embodiment of wherein a cover structure is in a collapsed or retracted orientation within an introductory instrument.
FIG. 14 is a longitudinal sectional view of the embodiment of FIG. 13 wherein the cover structure is in an expanded orientation.

Yet another preferred embodiment of the assembly for performing an occlusion of the left atrial appendage is represented in detail in FIGS. 13 and 14. More specifically, a delivery instrument is generally indicated as 200 and includes an introduction member 202 structured for introduction or passage into the heart in an operative position. The operative position of the delivery instrument 200 may include its direct communicating relation with the left atrial appendage, such as schematically represented with regard to the description of the different embodiments of FIGS. 12A-12C.

In addition, the delivery instrument 200 includes a positioning member 204 initially disposed telescopically within the interior of the introduction member 202 so as to be movable relative thereto. A cover structure 206 is initially connected to the distal end of the positioning member 204 so as to move therewith between an expanded orientation and a collapsed orientation as represented in FIGS. 13 and 14. As will be described in greater detail hereinafter, the cover structure 206 is removably connected to the positioning member 204 so as to be detached therefrom when the cover structure 206 is operatively disposed in closing relation to the entrance of the left atrial appendage 104, as schematically represented.

The selective detachment of the cover structure 206 from the positioning member 204 may be accomplished by an appropriate linkage or connector 226. It is emphasized that other connecting linkage may be utilized to facilitate the accurate position of the cover structure 206, when in the collapsed orientation, as well as the detachment of the delivery instrument 200 there from, when the cover structure 206 is operatively disposed in the aforementioned covering relation to the entrance and interior of the left atrial appendage 104. As clearly represented in FIGS. 13 14, the cover structure 206 includes a plurality of ribs 208 each formed of a material having sufficient flexibility to provide an "inherent bias" thereto, which facilitates their "automatic" disposition from the collapsed orientation of FIG. 13 into the expanded orientation of FIG. 14.

Accordingly, the collapsed orientation of the cover structure 206 comprises the plurality of ribs 208 being disposed in substantially longitudinal alignment with one another and with the length and/or central axis of the interior lumen of the delivery instrument 200. However, upon disposition of the cover structure 206 through the open end 202' of the lumen the inherent bias associated with each of the plurality of ribs 208 will force them into the expanded orientation comprising a radially outward, spaced apart orientation as represented. Additional features of the cover structure 206 include a central hub 210 interconnected to and disposed in interconnecting relation with each of the plurality of flexible material ribs 208. Therefore, the aforementioned expanded orientation of the cover member 206 may be further defined by the plurality of ribs 208 extending radially outward from the hub 210 in spaced apart orientation as clearly represented in FIG. 15.

Features of the cover structure 206 comprise the inclusion of the plurality of gripping members 212 connected to free or outer distal ends 208' of at least some of the plurality of ribs 208. The gripping members 212 may have a pointed or other appropriate configuration to facilitate the penetration of the left atrial appendage 104 in an area adjacent to the entrance thereof as also schematically represented in the embodiments of FIGS. 8A through 8C. Further, each of the gripping members 212 is formed of a material having sufficient flexibility to also include the aforementioned "inherent bias".

Other structural features of the cover structure 206 include a facing material or structure 218 disposed in covering relation to the plurality of ribs 208 when in either the expanded or the collapsed orientations, as described above. Moreover, the facing material 218 may be formed of a Dacron® or other flexible and liquid impermeable material. The flexibility of the facing material 218 facilitates its movement in connected, covering relation to the plurality of ribs 208 as they move and/or are positioned between the collapsed and the expanded orientations.

Yet another preferred embodiment of the present invention is represented in FIGS. 15 through 20 and is directed to a closure system and method for closing and at least partially sealing a tissue opening 400 in the tissue 402 of a patient involved in a surgical procedure. As will be explained in greater detail hereinafter, the tissue opening 400 referred to will typically be formed in the human tissue 402 of the body and may include the internal organs. Further, the tissue opening 402 is formed for the purpose of facilitating the entry and/or positioning of one or more instruments relative to a surgical site, dependent on the surgical procedure being performed. By way of example, repair of the heart may involve entry of the myocardium for purposes of facilitating the entry and positioning of different instruments used to accomplish a surgical procedure on the heart. Further by way of example, correcting the function or repair of the mitral valve may involve the entry of the instrument through the atrial wall of the left atrium. This may be accomplished by the forming of an opening in the atrial wall of sufficient size and location to pass surgical instruments there through into operative relation with the mitral valve and/or the leaflets associated therewith. However, when the surgical procedure is completed and the performing instruments have been removed from the interior of the left atrium or other portions of the heart, the tissue opening must be closed and/or sealed to facilitate proper functioning of the heart, after the surgical procedure.

Accordingly, the closure system comprises a closure assembly 300 and its method of use facilitates the closure and at least partial sealing of the tissue opening 402 in various tissue parts 400 of the human body. It is emphasized that the closure assembly 300 of the present invention is not limited to tissue openings formed in the wall of the heart, but may be used to facilitate the closure of tissue openings in various portions of the patient's body.

Figure 15:
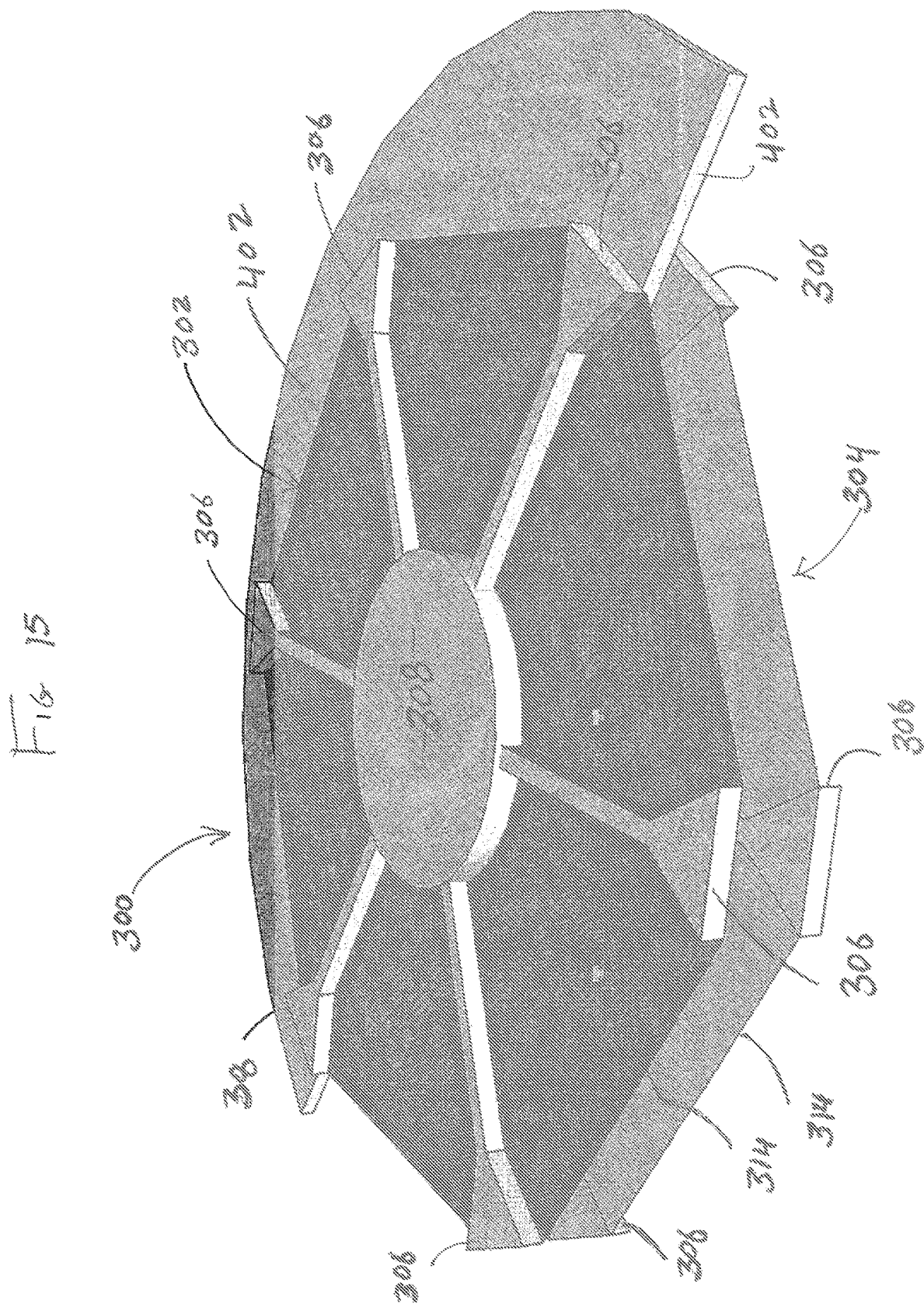
FIG. 15 is a perspective view in schematic form of yet another preferred embodiment of the closure system and closure assembly of the present invention.
Figure 16:
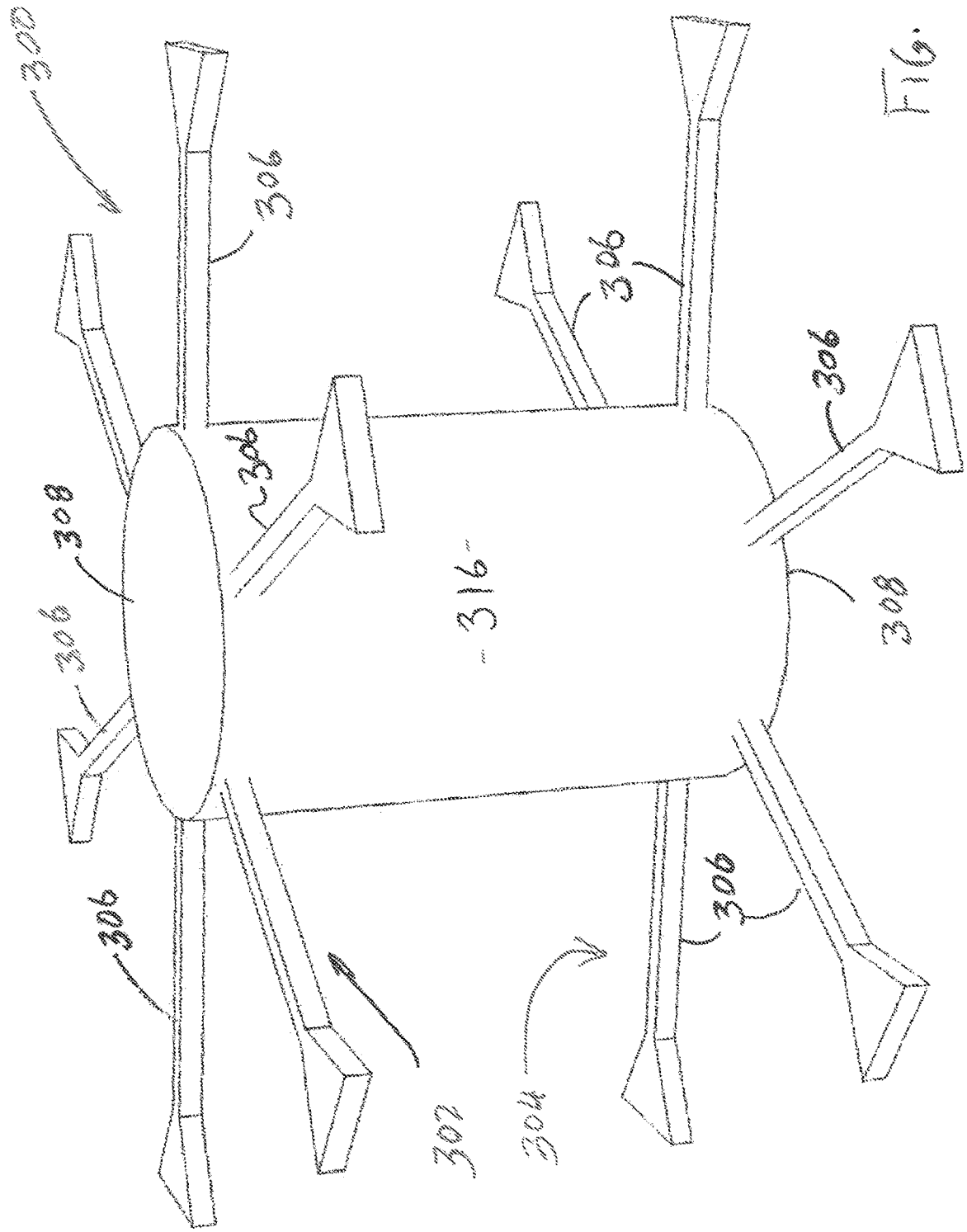
FIG. 16 is a perspective view in schematic form of the embodiment of the closure assembly of FIG. 15 in an operative, expanded orientation, but absent a cover material normally associated therewith.

In more specific terms, and with initial primary reference to FIGS. 15 and 16, the closure system includes the closure assembly generally indicated as 300. The closure assembly 300 includes at least a first closure member, generally indicated as 302 and a second closure member, generally indicated as 304. In at least one structural modification of the closure assembly 300, both the first and second closure members, 302 and 304 respectively, may be similarly or substantially equally structured to include a "biased construction". In the embodiment represented in FIGS. 15 through 20, such a biased construction may include a plurality of spring-like fingers or ribs 306 interconnected to a hub or a substantially central interconnecting portion 308. The hub or interconnecting portion 308 may be typically, but not necessarily exclusively, located at a central portion of each of the first and second closure members 302 and 304. Each of the plurality of fingers or ribs 306 is formed from an inherently biased material. As a result the fingers 306 of the closure members 302 and 304 may be selectively disposed in an expanded orientation, as represented in FIGS. 15, 16, and 20 or in a retracted orientation, as represented in FIG. 17 and at least partially represented in FIGS. 18 and 19.

Moreover, when the plurality of fingers 306 are in the expanded orientation the inherent bias of the material from which they are formed will facilitate their being normally biased, substantially radially outward from the hub or central portion 308 in spaced relation to one another. However, the inherent bias and flexibility of the material of the fingers 306 also facilitate their selective disposition into the retracted orientation. In the retracted orientation, the plurality of fingers 306 are disposed inwardly, substantially towards one another so as to assume a dimension sufficient to be movably disposed within a lumen 310 of a catheter or other introductory instrument 312. When in the expanded orientation of FIGS. 15, 16 and 20, the transverse dimension of each of the closure members 302 and 304 is greater than the diameter or transverse dimension of the tissue opening 400 being closed. As a result, the outer periphery of each of the first and second closure members 302 and 304 extend beyond the outer periphery of the tissue opening 400 and, when disposed in closing relation thereto as represented in FIG. 20, the first and second closure members 302 and 304 will overlie, cover and at least partially seal the tissue opening. Accordingly, when each the first and second closure members 302 and 304 include a base or frame portion comprising the plurality of spring-like fingers 306, the dimension and disposition of the plurality of fingers 306 of each of the first and second closure members 302 and 304 are such as to collectively define a transverse dimension greater than that of the tissue opening 400 being closed, when the closure members 302 and 304 are in the expanded orientation.

Additional features associated with each of the closure members 302 and 304 include a cover material or facing material 314 connected to and extending over the plurality of fingers or ribs 306. Further, the cover 314 of each closure members 302 and 304 is formed of a flexible material such as, but not limited to, Dacron. While the actual material from which the cover 314 may vary, at least one common characteristic thereof should include sufficient flexibility to move with the plurality of fingers or ribs 306 of a corresponding one of the closure members 302 and 304. Therefore, the cover material or facing 314 may be attached to the plurality of fingers 306 in a manner which facilitates the movement of the cover 314 with the plurality of fingers 306, between the aforementioned retracted orientation and expanded orientation. For purposes of clarity, the cover or facing material 314 is not represented in each of the FIGS. 16-19, in order that the remaining structural components and operative features of the closure assembly 300 may be clearly and accurately disclosed and described. However, in practice and as intended for use, the cover or facing 314 or its structural equivalent is connected to the plurality of fingers 306 or other structure of the frame or base of the prospective closure members 302 and 304 and movable there with between the retracted and expanded orientations and as the closure members 302 and 304 are disposed into the closing relation to the tissue opening 400. Further, as clearly represented in FIG. 20, a covering and confronting relation of the opposite open ends of the tissue opening 400 may be accomplished by the cover or facing material 314, so as to accomplish the closing and at least partial sealing of the tissue opening 400 formed in the human (or animal) tissue 402 associated with the surgical procedure.

FIGS. 16 through 20 represent additional structural and operative features of the closure assembly 300 including the provision of a connector 316. The connector 316 is disposed in directly interconnecting relation between the first and second closure members 302 and 304 such as by interconnecting the hub or substantially central interconnecting portions 308 thereof. Moreover, the connector 316 may be formed of a rigid, semi rigid, and/or flexible material. In addition, the transverse and longitudinal dimension of the connector 316 may vary, in order to accommodate the interior dimensions of the lumen 310 and accordingly the tissue opening 400. The dimensions of the connector 316 may also be predetermined to define an intended spacing between the first and second closure members 302 and 304, whether in the expanded or retracted orientations. In addition, the direct interconnection between the closure members 302 and 304 by the connector 316 facilitates their concurrent movement within the lumen 310 of the introductory instrumentation 312, as the closure assembly 300 passes through the lumen 310, along the length of the introductory instrument 312 towards and out of the open end 310'.

As will be explained in greater detail hereinafter, independent and successive deployment of each of the closure members 302 and 304 out of the open end 310' and successively into a closing relation with the tissue opening 400 of the tissue 402 in which it is formed. As explained in greater detail hereinafter, the "closing relation" of the closure assembly 300, as represented in FIGS. 15 and 20, relative to the tissue opening 400 will be at least partially defined by both the first and second closure members 302 and 304 being concurrently disposed in the expanded orientation. As also represented in FIGS. 15 and 20, the tissue 402 is disposed in sandwiched relation between the closure members 302 and 304. Therefore, the closing relation of the closure assembly 300 comprises the closure members 302 and 304 being disposed on opposite sides 402' and 402" of the tissue 400 in overlying, covering, closing and at least partially sealing engagement and/or confronting disposition with the opposite open ends of the tissue opening 400.

With primary reference to FIGS. 17 through 19, the operative and structural features of the closure assembly 300 and its method of use and positioning are clearly demonstrated. (For purposes of clarity, the fingers of the first closure member 302 and the second closure member 304 are respectively designated as 306 and 306' in FIGS. 17 through 19.) More specifically, operatively positioning the closure assembly 300 includes it being disposed within the lumen 310. In order to conform to the interior dimensions of the lumen 310, the plurality of inherently biased fingers 306 and 306', of each closure member 302 and 304, are disposed into the retracted orientation, as represented. Further, while the inherent bias of the fingers 306 and 306' will tend to normally bias them into the radially outwardly expanded orientation, as represented in FIGS. 15-20, their positioning into the retracted orientation will sufficiently conform the closure members 302 and 304 to the dimensions of the interior of the lumen 310. As a result, movement of the closure assembly 300 along the length of the introductory instrument 312 and through the open and 310' of the lumen 310 is facilitated. Accordingly, when ready for disposition into a closing relation relative to the tissue opening 400, the closure assembly 300 is moved within the lumen 310 towards and through the open end 310', as schematically represented by directional arrow 404, once the catheter or introductory instrument 312 first passes through the tissue opening 400, to be closed.

Once the open and 310' is disposed completely through the tissue opening 400, the closure assembly 300 is moved along the length of the lumen 310 until the first closure member 302 passes outwardly from the open and 310'. Once deployed from interior of the lumen 310, through the open and 310', the inherent bias of the fingers 306 will result in an "automatic" expansion of the first closure member 302 into the expanded orientation as clearly represented in FIGS. 18 and 19. However, the fingers 306' of the second closure member 304 will still be disposed on the interior of the lumen 310. Therefore, while the first closure member 302 is in the expanded orientation on one side 402' of the tissue 402, as also represented in FIGS. 18 and 19, the introductory instrument 312 will be withdrawn back through the tissue opening 400, as schematically represented by directional arrow 405 in FIG. 19. The open end 310' of the lumen 310 will then be disposed on the opposite side 402" of the tissue 402, relative to the positioning of the first closure member 302.

Therefore, while the first closure member 302 is in the expanded orientation on a first or "inner side" 402' of the tissue 402, the catheter or instrument 312 will be passed back through the tissue opening 400 until it reaches the opposite side 402". Once the opening 310' is located on the opposite side 402" of the tissue 402, the second closure member 304 and the introductory instrument 312 are respectively and/or relatively moved, such that the second closure member 304 exits the open end 310'. As a result, once the closure member 304 has passed through the open end 310', the inherently biased fingers 306' will also be disposed into the expanded orientation. As a result, the closure assembly 300 will assume the expanded orientations of the first and second closure members 302 and 304 as represented in FIGS. 15 and 20. Therefore, the aforementioned "closing relation" of the closure assembly 300 will be at least partially defined by each of the first and second closure members 302 and 304 being located on opposite sides 402' and 402" of the tissue 402, as well as on opposite sides or opposite open ends of the tissue opening 400. Concurrently, the connector 316 will be disposed through and within the tissue opening 400, while the first and second closure members 302 and 304 will be disposed in covering, closing and/or at least partially sealing relation to the opposite ends of the tissue opening 400.

It is again emphasized that while not disclosed or represented in FIGS. 18 and 19, the cover or facing material 314 will be attached to, mounted on and/or be a part of each of the closure members 302 and 304, such as by being attached to the fingers 306 and 306' thereof. The presence of the cover or facing material 314 in overlying relation to the plurality of fingers 306 and 306' facilitates the covering, closing at least partial sealing of the tissue opening 400, as should be apparent. Accordingly, the biased construction of the first and second closure members 302 and 304 and the interconnection in at least partially spaced relation to one another facilitates the concurrent disposition of the first and second closure members 302 and 304 respectively with one another, while both are disposed within the lumen 310, as represented in FIG. 17. In addition, the biased construction and interconnection of the closure members 302 and 304 in at least partially spaced relation to one another also facilitates the independent and successive movement and positioning of the first and second closure members 302 and 304, relative to one another, as they independently and successively expand into the closing relation to the tissue opening 400, on opposite sides of the tissue 402' and 402" respectively. Further, the independent and successive disposition of the first and second closure members 302 and 304 into the expanded orientation, as represented in FIGS. 15 and 20 will occur as each of the closure members 302 and 304 are deployed from or exit the open and 310' of the lumen 310.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An introduction assembly for the insertion of medical instruments through a thoracic passage in an intercostal space of a thoracic wall and into a targeted atrium of a heart, said introduction assembly comprising:

a puncturing instrument, comprising a puncturing needle or a lancet, dimensioned and structured to form an entry site into the targeted atrium and corresponding pericardial bag, an elongated sheath including a central lumen, said sheath and said puncturing instrument both including a length sufficient to extend concurrently and continuously, in unison, from an exterior of the thoracic wall through the thoracic passage and through the entry site;

said sheath including a distal end, said puncturing instrument disposed within said sheath in outwardly protruding relation from said distal end of said sheath during movement of said sheath and said puncturing instrument through the thoracic passage in the thoracic wall and the entry site, a buffer disposed on said sheath in segregating relation between said distal end of said sheath and a remainder of said sheath, said buffer structured to limit insertion of said distal end of said sheath into the targeted atrium through the entry site thereby defining a maximum intracardial length which said distal end of said sheath extends into the targeted atrium during a procedure, at least a distal end of said sheath being at least partially flexible, a closure assembly disposable in an operative position in closing relation to the entry site in the targeted atrium subsequent to removal of said sheath therefrom, said sheath and said central lumen dimensioned and configured to receive and facilitate passage therethrough of instrumentation dedicated to perform predetermined cardiac maneuvers, a securing assembly disposed and structured to removably secure said buffer interiorly of the thoracic wall and on an exterior of the targeted atrium, and said securing assembly comprising a vacuum source, said buffer connected in fluid communication with said vacuum source and structured to exert a securing negative pressure force on an exterior of the pericardial bag.

2. An introduction assembly as recited in claim 1 wherein said buffer is further structured for confronting disposition with an exterior portion of the pericardial bag corresponding to the entry site.

3. An introduction assembly as recited in claim 2 wherein said buffer is disposed on said sheath at a location to at least partially define said maximum intracardial length.

4. An introduction assembly as recited in claim 1 further comprising a valve assembly connected to a proximal end of said sheath, externally of the thoracic passage and in flow restricting relation to said central lumen.

5. An introduction assembly as recited in claim 4 wherein said valve assembly is operatively structured to restrict fluid flow through said proximal end of said sheath at least during operative positioning of insertion and removal of dedicated instrumentation.

6. An introduction assembly as recited in claim 1 wherein said closure assembly comprises a first segment and a second segment respectively and concurrently disposable interiorly and exteriorly of the entry site and in substantially closing relation thereto.

7. An introduction assembly as recited in claim 6 wherein said operative position of said closure assembly comprises said first and second segments respectively disposed in confronting relation to the entry site on an interior and exterior of the targeted atrium.

8. An introduction assembly as recited in claim 1 wherein said closure assembly is disposable in a substantially collapsed orientation of sufficient dimension to pass through said central lumen of said sheath to the entry site.

9. An introduction assembly as recited in claim 8 wherein said closure assembly is disposable into an expanded orientation.

10. An introduction assembly as recited in claim 9 wherein said closure assembly comprises a first segment and a second segment respectively and concurrently disposable interiorly and exteriorly of the entry site; each of said first and second segments disposable into said substantially collapsed orientation and said expanded orientation.

11. An introduction assembly as recited in claim 10 wherein each of said first and second segments includes an inherently biased construction facilitating disposition thereof into said expanded orientation and said operative position, upon an exiting thereof from said sheath.

12. An introduction assembly as recited in claim 1 wherein said puncturing instrument comprises a lancet at least partially formed of a flexible material and cooperatively dimensioned with said sheath to facilitate passage of at least a portion of said lancet into operative engagement with the targeted atrium.

13. An introduction assembly as recited in claim 12 wherein said lancet comprises a blade disposed at the distal end thereof, said blade selectively disposed between a retracted position, within said sheath, and an extended position, protruding outwardly from said distal end of said sheath.

14. An introduction assembly as recited in claim 13 wherein said lancet further comprises an activating structure, disposed exteriorly of said sheath and operative from a proximal end of said lancet, said activating structure operative to selectively dispose said blade between said retracted position and said extended position.

15. An introduction assembly as recited in claim 1 further comprising a fluid connection disposed at least partially on said sheath in fluid communication between said vacuum source and said buffer.

16. An introduction assembly as recited in claim 1 wherein said buffer includes a collapsible construction.

17. An introduction assembly as recited in claim 1 wherein said buffer comprises a substantially annular configuration connected to an exterior of said sheath and extendable transversely outward therefrom into movement restricting engagement with an exterior of the pericardial bag.

18. An introduction assembly as recited in claim 1 wherein said buffer comprises a plurality of pads connected to an exterior of said sheath and extendable transversely outward therefrom into interruptive, movement restricting engagement with an exterior of the pericardial bag.

19. An introduction assembly as recited in claim 1 further comprising a stabilizing assembly disposable in interconnecting relation between said sheath and an adjacent portion of the thoracic passage exteriorly of the thoracic wall.

20. An introduction assembly as recited in claim 19 wherein said stabilizing assembly includes an angle compensating structure operative to accommodate an angular orientation of said sheath relative to the thoracic passage.

21. An introduction assembly as recited in claim 19 wherein said stabilizing assembly is structured for removable attachment to a skin surface disposed adjacent to the thoracic passage.

22. An introduction assembly for the insertion of medical instruments through a thoracic passage in an intercostal space of a thoracic wall and into a targeted atrium of a heart, said introduction assembly comprising:

an elongated sheath having a central lumen and a puncturing instrument comprising a lancet assembly, including a blade, disposed and structured to form an entry site into the targeted atrium and corresponding pericardial bag, said puncturing instrument movably and removably disposed within said central lumen, said sheath and said puncturing instrument both including a length sufficient to extend, in unison, concurrently and continuously from an exterior of the thoracic wall through the thoracic passage and through the entry site;

said sheath including a distal end having a maximum intracardial length and being at least partially flexible, at least at a portion thereof being configured to engage said entry site during a procedure, a buffer disposed on said sheath in segregating relation between said distal end of said sheath and a remainder of said sheath, said buffer structured to limit insertion of said distal end of said sheath into the targeted atrium through the entry site beyond said maximum intracardial length of said distal end of said sheath, said blade positioned at a distal end of said sheath and disposable between a retracted position, within said sheath, and an extended position, protruding outward from said distal end of said sheath, concurrently to a remainder of said lancet assembly remaining within said sheath, a stabilizing assembly connected to said sheath exteriorly of the thoracic wall and disposed and structured to stabilize said sheath relative to the thoracic passage, a securing assembly configured to connect to said sheath in interconnecting, securing relation between said sheath and an exterior of the targeted atrium, and structured to removably secure said buffer interiorly of the thoracic wall and on an exterior of the targeted atrium, a closure assembly disposable in an operative position in closing relation to the entry site in the targeted atrium subsequent to removal of said sheath therefrom, said sheath and said central lumen dimensioned and configured to receive and facilitate passage therethrough of instrumentation dedicated to perform predetermined cardiac maneuvers upon removal of said puncturing instrument, and said securing assembly comprising a vacuum source, said buffer connected in fluid communication with said vacuum source and structured to exert a securing negative pressure force on an exterior of the pericardial bag.

23. An introduction assembly for the insertion of medical instruments through a thoracic passage in an intercostal space of a thoracic wall and into a targeted atrium of a heart, said introduction assembly comprising:

a puncturing instrument, dimensioned and structured to form an entry site into the targeted atrium and corresponding pericardial bag, an elongated sheath including a central lumen, said sheath and said puncturing instrument both including a length sufficient to extend concurrently and continuously, in unison, from an exterior of the thoracic wall through the thoracic passage and through the entry site;

said sheath including a distal end, said puncturing instrument disposed within said sheath in outwardly protruding relation from said distal end of said sheath during movement of said sheath and said puncturing instrument through the thoracic passage in the thoracic wall and the entry site, a buffer disposed on said sheath in segregating relation between said distal end of said sheath and a remainder of said sheath, said buffer structured to limit insertion of said distal end of said sheath into the targeted atrium through the entry site thereby defining a maximum intracardial length which said distal end of said sheath extends into the targeted atrium during a procedure, at least a distal end of said sheath being at least partially flexible, a closure assembly disposable in an operative position in closing relation to the entry site in the targeted atrium subsequent to removal of said sheath therefrom, said sheath and said central lumen dimensioned and configured to receive and facilitate passage therethrough of instrumentation dedicated to perform predetermined cardiac maneuvers, and a stabilizing assembly disposable in interconnecting relation between said sheath and an adjacent portion of the thoracic passage exteriorly of the thoracic wall, a securing assembly disposed and structured to removably secure said buffer interiorly of the thoracic wall and on an exterior of the targeted atrium, and said securing assembly comprising a vacuum source, said buffer connected in fluid communication with said vacuum source and structured to exert a securing negative pressure force on an exterior of the pericardial bag.

* * * * *